United States Patent
Iida et al.

(10) Patent No.: US 7,253,299 B2
(45) Date of Patent: Aug. 7, 2007

(54) PROCESS FOR PURIFYING N2-(1(S)-ETHOXYCARBONYL-3-PHENYLPROPYL)-N6-THIFLUOROACETYL-L-LYSINE

(75) Inventors: Yasuhiro Iida, Kakogawa (JP); Hajime Manabe, Amagasaki (JP); Yasuyoshi Ueda, Himeji (JP)

(73) Assignee: Kaneka Corporation, Tokyo (JP)

( * ) Notice: Subject to any disclaimer, the term of this patent is extended or adjusted under 35 U.S.C. 154(b) by 336 days.

(21) Appl. No.: 10/432,288

(22) PCT Filed: Jul. 10, 2002

(86) PCT No.: PCT/JP02/06990

§ 371 (c)(1),
(2), (4) Date: May 20, 2003

(87) PCT Pub. No.: WO03/006421

PCT Pub. Date: Jan. 23, 2003

(65) Prior Publication Data
US 2004/0147773 A1  Jul. 29, 2004

(30) Foreign Application Priority Data
Jul. 11, 2001  (JP) .............................. 2001-210399

(51) Int. Cl.
*C07C 229/00* (2006.01)
*C07C 51/42* (2006.01)

(52) U.S. Cl. .............................. 560/38; 560/39; 560/41; 562/494

(58) Field of Classification Search ................. 560/38, 560/39, 41; 562/494
See application file for complete search history.

(56) References Cited

U.S. PATENT DOCUMENTS 6,118,010 A * 9/2000 Ueda et al. ................. 548/532

FOREIGN PATENT DOCUMENTS

| EP | 239062 A2 | 9/1987 |
| EP | 336368 A2 | 10/1989 |

* cited by examiner

*Primary Examiner*—Taylor Victor Oh
(74) *Attorney, Agent, or Firm*—Sughrue Mion, PLLC

(57) ABSTRACT

A process for purifying $N^2$-(1(S)-ethoxycarbonyl-3-phenylpropyl)-$N^6$-trifluoroacetyl-L-lysine which comprises subjecting $N^2$-(1(S)-ethoxycarbonyl-3-phenylpropyl)-$N^6$-trifluoroacetyl-L-lysine contaminated with impurities to crystallization from a solvent comprising a water-soluble non-protic organic solvent, thereby removing the impurities into the mother liquor and giving crystals of $N^2$-(1(S)-ethoxycarbonyl-3-phenylpropyl)-$N^6$-trifluoroacetyl-L-lysine, according to which $N^2$-(1(S)-ethoxycarbonyl-3-phenylpropyl)-$N^6$-trifluoroacetyl-L-lysine having a high quality can be obtained in a high yield and a high productivity and which is suitable for practice on an industrial scale.

22 Claims, 6 Drawing Sheets

PROCESS FOR PURIFYING N2-(1(S)-ETHOXYCARBONYL-3-PHENYLPROPYL)-N6-THIFLUOROACETYL-L-LYSINE

TECHNICAL FIELD

The present invention relates to a process for purifying $N^2$-(1(S)-ethoxycarbonyl-3-phenylpropyl)-$N^6$-trifluoroacetyl-L-lysine of the formula (1):

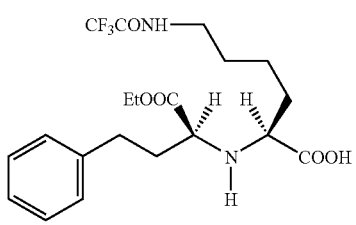

(1)

$N^2$-(1(S)-ethoxycarbonyl-3-phenylpropyl)-$N^6$-trifluoroacetyl-L-lysine is a compound very useful as intermediates for the production of drugs and medicines, particularly as an intermediate for the production of antihypertensive agent (angiotensin converting enzyme inhibitor) lysinopril.

BACKGROUND ART

As a process of the synthesis of $N^2$-(1(S)-ethoxycarbonyl-3-phenylpropyl)-$N^6$-trifluoroacetyl-L-lysine are hitherto known (a) a process wherein after conducting a Michael addition reaction of $N^6$-trifluoroacetyl-L-lysine to ethyl β-benzoylacrylate, carbonyl group in the benzoyl portion is converted into methylene group by catalytic reduction (JP-B-4-4308), (b) a process wherein ethyl 2-oxy-4-phenylbutyrate and $N^6$-trifluoroacetyl-L-lysine are subjected to reductive amination (CN-B-1053437), and the like.

Besides the desired $N^2$-(1(S)-ethoxycarbonyl-3-phenylpropyl)-$N^6$-trifluoroacetyl-L-lysine, various impurities having analogous structures are by-produced or remain in the above-mentioned processes.

These impurities are, for instance, the diastereomer, i.e., $N^2$-(1(R)-ethoxycarbonyl-3-phenylpropyl)-$N^6$-trifluoroacetyl-L-lysine of the formula (2):

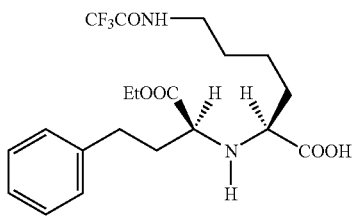

(2)

a cyclohexyl derivative, i.e., $N^2$-(1(S)-ethoxycarbonyl-3-cyclohexyl-propyl)-$N^6$-trifluoroacetyl-L-lysine of the formula (3):

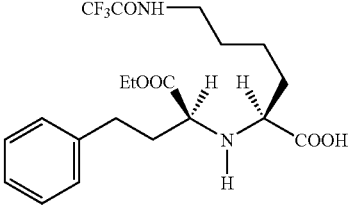

(3)

a carboxyl derivative, i.e., $N^2$-(1(S)-carboxy-3-phenylpropyl)-$N^6$-trifluoroacetyl-L-lysine of the formula (4):

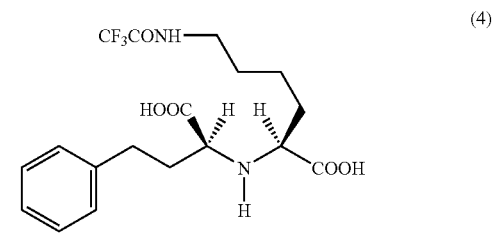

(4)

an ester derivative, i.e., $N^2$-(1(S)-ethoxycarbonyl-3-phenylpropyl)-$N^6$-trifluoroacetyl-L-lysine ester of the formula (5):

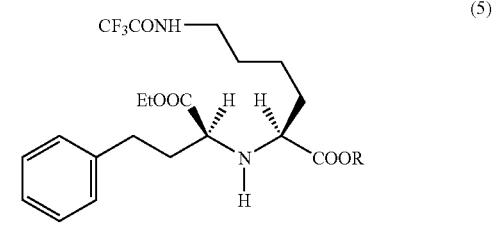

(5)

wherein R is an alkyl group, ethyl phenylbutyrate, and the like.

The diastereomer (2) is produced when the stereoselectivity of the reaction is insufficient. The cyclohexyl derivative (3) is produced by hydrogenation of benzene ring when the catalytic reduction is conducted. The carboxyl derivative (4) is produced by hydrolysis or by cleavage of the ester moiety during the catalytic reduction. The ester derivative (5) is a compound that the terminal carboxyl group of the desired product is converted into an ester group, and is produced by a side reaction. In the formula (5), R denotes an alkyl group such as methyl group or ethyl group, especially a lower alkyl group having 1 to 4 carbon atoms. Also, ethyl phenylbutyrate is produced by reduction of ethyl β-benzoylacrylate.

Needless to say, incorporation of these structure analogous impurities and so on into the product $N^2$-(1(S)-ethoxycarbonyl-3-phenyl-propyl)-$N^6$-trifluoroacetyl-L-lysine should be prevented as much as possible, and for this purpose, a good purification process is required.

As a process of the purification of $N^2$-(1(S)-ethoxycarbonyl-3-phenylpropyl)-$N^6$-trifluoroacetyl-L-lysine is hitherto known a process wherein crystallization is conducted from an ethanol/water mixed solvent whereby the diastereomer is removed (JP-B-4-4308).

However, as a result of present inventors' investigation, it was found that this purification process has large problems on industrial production that the physical properties of the obtained crystals are bad, the filtering property is bad, the filtered cake cracks and therefore it is not possible to conduct washing, resulting in low quality, the obtained wet matter has a high liquid content and therefore is hard to be dried, and the crystallization concentration is not necessarily high.

Accordingly, an object of the present invention is to provide a process of the purification suitable for practice on an industrial scale for obtaining $N^2$-(1(S)-ethoxycarbonyl-3-phenylpropyl)-$N^6$-trifluoroacetyl-L-lysine having a high quality, namely high purity and good physical properties of crystals, in a high yield and a high productivity.

DISCLOSURE OF INVENTION

The present inventors have found, as a result of intensive study to solve the problem, that by carrying out the crystallization from a water-soluble non-protic organic solvent or a solvent containing a water-soluble non-protic organic solvent, the operability and productivity based on physical properties of crystals and the like can be remarkably improved, and besides, the purification can be achieved in satisfactory high yield and quality. In addition, it has been found that it is very preferable to use, as a solvent containing a water-soluble non-protic organic solvent, a water-soluble non-protic organic solvent/water mixed solvent with the use of water as an auxiliary solvent, and to carry out the crystallization therefrom, and further that polymorphism and crystal habit which occur when crystallizing from a water-soluble non-protic organic solvent/water mixed solvent can be controlled to give crystals having preferable polymorphs and crystal habit.

Thus, in accordance with the present invention, there is provided a process for purifying $N^2$-(1(S)-ethoxycarbonyl-3-phenylpropyl)-$N^6$-trifluoroacetyl-L-lysine of the formula (1):

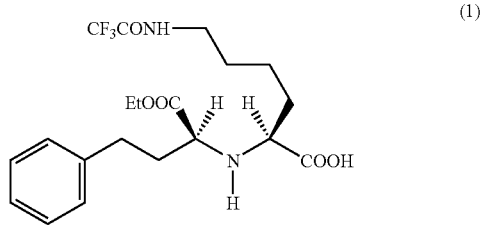

comprising subjecting $N^2$-(1(S)-ethoxycarbonyl-3-phenylpropyl)-$N^6$-trifluoroacetyl-L-lysine contaminated with impurities to crystallization from a water-soluble non-protic organic solvent or a solvent containing a water-soluble non-protic organic solvent, thereby removing the impurities into the mother liquor and giving crystals of $N^2$-(1(S)-ethoxycarbonyl-3-phenylpropyl)-$N^6$-trifluoroacetyl-L-lysine.

Further, the present invention provides crystals of a hydrate of $N^2$-(1(S)-ethoxycarbonyl-3-phenylpropyl)-$N^6$-trifluoroacetyl-L-lysine which give crystals showing a powder X-ray diffraction pattern shown in FIG. 1 when said hydrate crystals are dried at 40° C. under a pressure of not higher than 5 mmHg to remove the crystal water.

The present invention also provides crystals of a hydrate of $N^2$-(1(S)-ethoxycarbonyl-3-phenylpropyl)-$N^6$-trifluoroacetyl-L-lysine which provide crystals showing a powder X-ray diffraction pattern shown in FIG. 2 when said hydrate crystals are dried at 40° C. under a pressure of not higher than 5 mmHg to remove the crystal water.

The present invention further provides crystals of a hydrate of $N^2$-(1(S)-ethoxycarbonyl-3-phenylpropyl)-$N^6$-trifluoroacetyl-L-lysine which provide crystals showing a powder X-ray diffraction pattern shown in FIG. 3 when said hydrate crystals are dried at 40° C. under a pressure of not higher than 5 mmHg to remove the crystal water.

Further, the present invention provides crystals of a hydrate of $N^2$-(1(S)-ethoxycarbonyl-3-phenylpropyl)-$N^6$-trifluoroacetyl-L-lysine having a crystal habit composed mainly of a crystalline form that the minor axis is not more than about 10 μm and the major axis is not more than about 50 μm, or their dried crystals (including non-hydrate crystals).

The present invention also provides crystals of a hydrate of $N^2$-(1(S)-ethoxycarbonyl-3-phenylpropyl)-$N^6$-trifluoroacetyl-L-lysine having a crystal habit composed mainly of a crystalline form that the minor axis is not more than about 30 μm and the major axis is about 200 μm, or their dried crystals (including non-hydrate crystals).

In the present invention, the powder X-ray diffraction data were obtained by using an X-ray diffractometer RAD-γA made by Rigaku Denki Kabushiki Kaisha and measuring the angle of diffraction at 2θ with CuKα radiation.

BEST MODE FOR CARRYING OUT THE INVENTION

Figure 1:
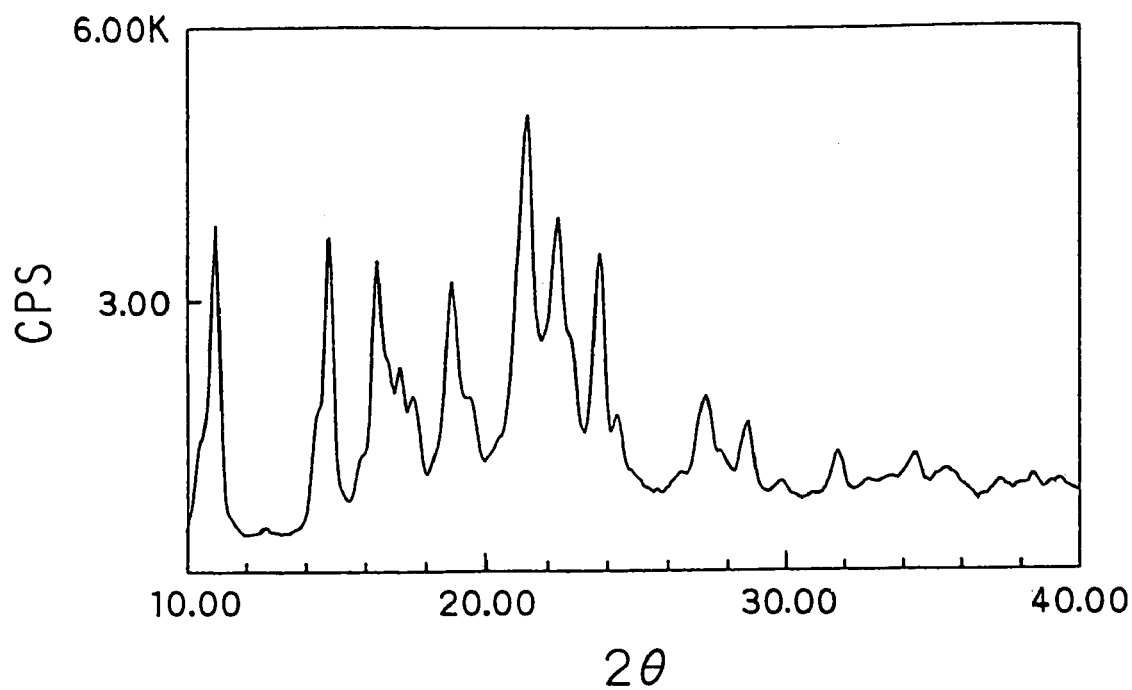
FIG. 1 is a powder X-ray diffraction pattern of crystals of I form of $N^2$-(1(S)-ethoxycarbonyl-3-phenylpropyl)-$N^6$-trifluoroacetyl-L-lysine.
Figure 2:
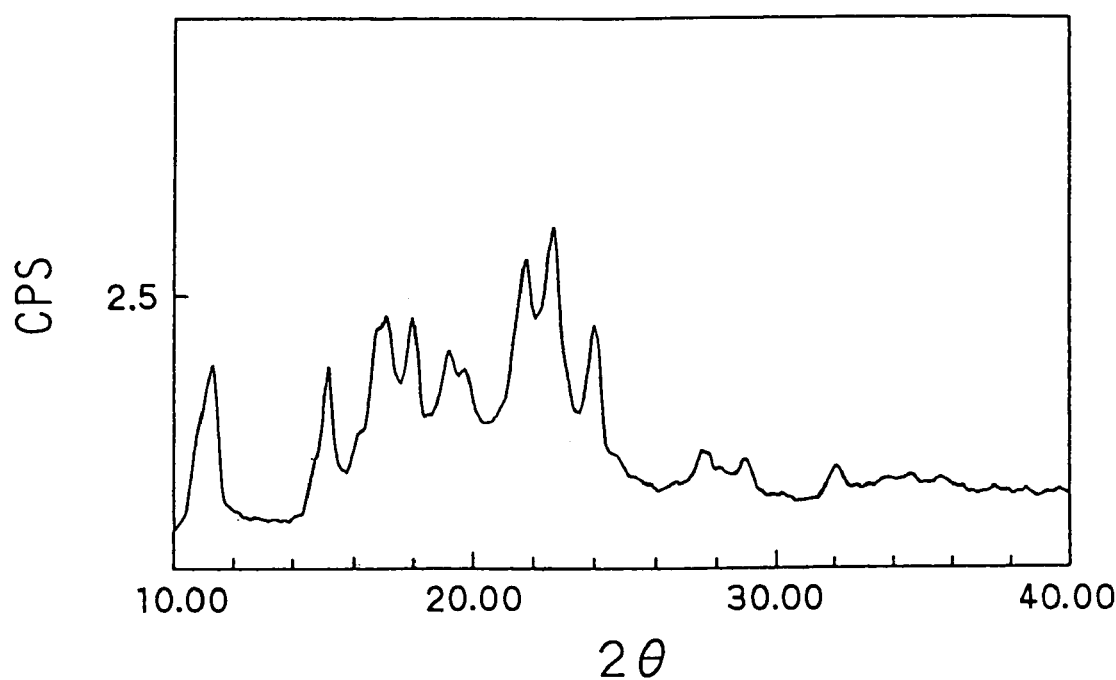
FIG. 2 is a powder X-ray diffraction pattern of crystals of II form of $N^2$-(1(S)-ethoxycarbonyl-3-phenylpropyl)-$N^6$-trifluoroacetyl-L-lysine.
Figure 3:
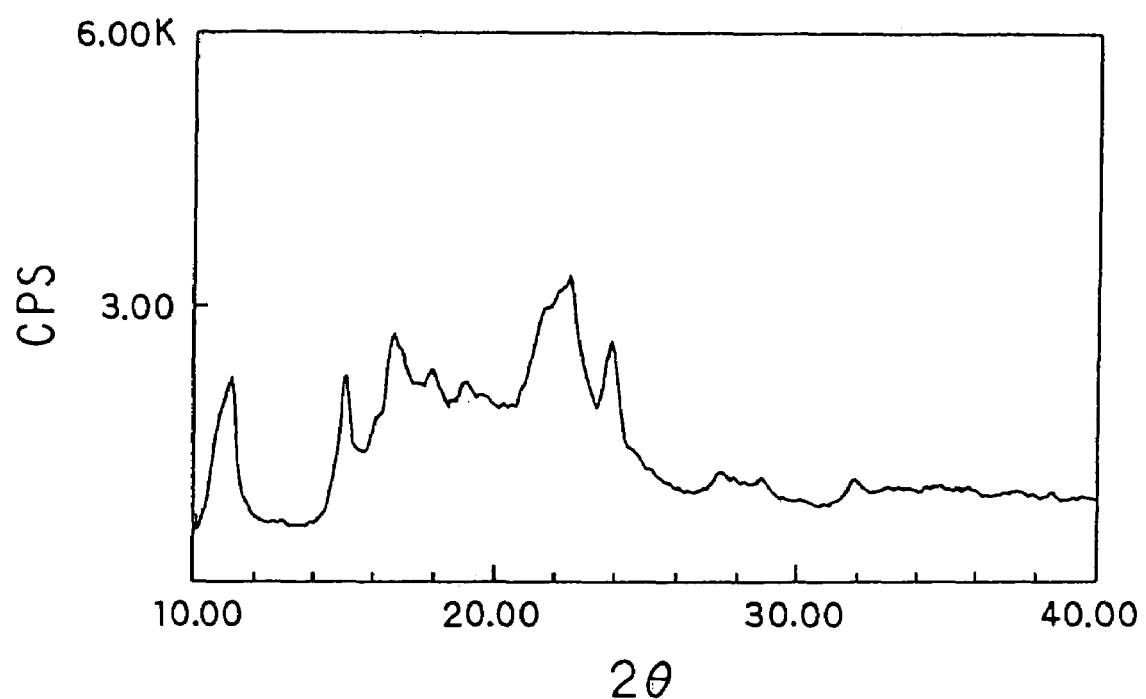
FIG. 3 is a powder X-ray diffraction pattern of crystals of III form of $N^2$-(1(S)-ethoxycarbonyl-3-phenylpropyl)-$N^6$-trifluoroacetyl-L-lysine.

The purification process of the present invention comprises crystallizing $N^2$-(1(S)-ethoxycarbonyl-3-phenylpropyl)-$N^6$-trifluoroacetyl-L-lysine from a solvent comprising a water-soluble non-protic organic solvent.

In the present invention, in order to obtain $N^2$-(1(S)-ethoxycarbonyl-3-phenylpropyl)-$N^6$-trifluoroacetyl-L-lysine with high quality, namely high purity and good physical properties of crystals, in a high yield and a high productivity from $N^2$-(1(S)-ethoxycarbonyl-3-phenylpropyl)-$N^6$-trifluoroacetyl-L-lysine contaminated with impurities, the crystallization is carried out from a water-soluble non-protic organic solvent alone or a solvent containing a water-soluble non-protic organic solvent.

The water-soluble non-protic organic solvent is not particularly limited. Examples thereof are, for instance, acetonitrile, acetone, methyl ethyl ketone, tetrahydrofuran, dioxane, and the like. Of these, acetonitrile is the most preferable.

In the present invention, the crystallization can be carried out from solvent systems containing a water-soluble non-protic organic solvent wherein other auxiliary solvents are used together with the water-soluble non-protic organic solvent. The auxiliary solvents are used for the purpose of improving conditions, such as solubilities of $N^2$-(1(S)-ethoxycarbonyl-3-phenylpropyl)-$N^6$-trifluoroacetyl-L-lysine and coexisting impurities, effect of removing impurities, physical properties of crystals and the like, which exert an influence on yield and quality.

As the auxiliary solvents are preferred those having a miscibility with the water-soluble non-protic organic solvents. The auxiliary solvents are not particularly limited, but include, for instance, hydrocarbons, fatty acid esters, ethers, ketones, alcohols, water, and the like. The hydrocarbons are preferably aliphatic hydrocarbons having 5 to 10 carbon atoms, aromatic hydrocarbons having 6 to 12 carbon atoms and halogenated hydrocarbons having 1 to 6 carbon atoms, and are more preferably aliphatic hydrocarbons having 6 to 8 carbon atoms, aromatic hydrocarbons having 7 to 10 carbon atoms and halogenated hydrocarbons having 1 to 4 carbon atoms. The fatty acid esters are preferably formic acid esters and acetic acid esters, more preferably esters of formic acid or acetic acid with alcohols having 1 to 4 carbon atoms. The ethers are preferably ethers having 4 to 10 carbon atoms, more preferably ethers having 5 to 8 carbon atoms. The ketones are preferably ketones having 5 to 10 carbon atoms, more preferably ketones having 5 to 8 carbon atoms. The alcohols are preferably alcohols having 1 to 8 carbon atoms, more preferably alcohols having 1 to 4 carbon atoms. Examples of the hydrocarbons are, for instance, an aliphatic hydrocarbon such as hexane, cyclohexane, heptane or methylcyclohexane; an aromatic hydrocarbon such as toluene or xylene; a halogenated hydrocarbon such as dichloromethane or 1,2-dichloroethylene. Examples of the fatty acid esters are an acetic acid ester such as ethyl acetate, isopropyl acetate, n-propyl acetate, t-butyl acetate, isobutyl acetate, n-butyl acetate or methyl acetate; and a formic acid ester such as ethyl formate or isopropyl formate. Examples of the ethers are methyl t-butyl ether, diisopropyl ether, and the like. Examples of the ketones are methyl isobutyl ketone, and the like. Examples of the alcohols are methanol, ethanol, 1-propanol, 2-propanol, and the like.

Water is particularly preferred as the auxiliary solvent. By using a water-soluble non-protic organic solvent in combination with water, the effect of removing impurities is further enhanced and the physical properties of crystals are also further improved.

The amount of auxiliary solvent used at the time of the crystallization varies depending on the kind of water-soluble non-protic organic solvent used, but is generally from 0 to 10 in terms of auxiliary solvent/water-soluble non-protic organic solvent ratio by volume. The upper limit of the volume ratio is preferably 2, more preferably 1 and the most preferably 0.5, and the lower limit of the volume ratio is preferably 0.05, more preferably 0.1. The preferable range of the volume ratio is from 0.05 to 2, more preferably from 0.05 to 1, further more preferably from 0.1 to 1, the most preferably from 0.1 to 0.5, and within this range the crystallization is suitably performed.

In the present invention, it is preferable from the viewpoints of yield, quality and the like to carry out the crystallization of $N^2$-(1(S)-ethoxycarbonyl-3-phenylpropyl)-$N^6$-trifluoroacetyl-L-lysine at a pH of 3 to 6, especially a pH of 3.5 to 5.5. In case that the pH of solution is too low or too high owing to coexistence of impurities or the like, the pH can be adjusted by using an acid (e.g., mineral acid such as hydrochloric acid or sulfuric acid) or a base (e.g., alkali metal hydroxide such as sodium hydroxide or lithium hydroxide).

In the present invention, it is preferable to carry out the crystallization of $N^2$-(1(S)-ethoxycarbonyl-3-phenylpropyl)-$N^6$-trifluoro-acetyl-L-lysine under forced flowing. From the viewpoint of giving a high quality, preferable is the flowing that the power required for agitation per unit volume is usually not less than about 1 $W/m^3$, preferably not less than about 10 $W/m^3$, more preferably not less than about 100 $W/m^3$, especially not less than about 1 $kW/m^3$. The forced flowing is provided to usually by rotation of agitating vanes (impellers), but it is not always required to use the agitating vanes so long as the flowing is obtained. For example, circulation of liquid or the like methods may be utilized.

The crystallization temperature is not particularly limited and, for example, the crystallization can be performed at a temperature of –20 to 100° C., preferably 0 to 80° C. From the viewpoint of quality (product purity and physical properties of crystals), it is more preferable to perform the crystallization under a heating condition for a large portion of the compound to be recovered, and usually the crystallization is performed at a temperature of not lower than about 20° C., preferably not lower than about 30° C.

The crystallization according to the present invention can be carried out by using at least one of general crystallization methods, i.e., cooling crystallization, neutralizing crystallization, concentrating crystallization (including crystallization by solvent replacement), etc. Usually, it is preferable to carry out the crystallization by means of at least one of cooling crystallization and concentrating crystallization. Cooling crystallization is particularly preferred.

In order to maximize the effects of the present invention, it is preferable to control the crystallization velocity, namely the amount of crystals produced per unit time, to minimize incorporation of impurities into the crystals of $N^2$-(1(S)-ethoxycarbonyl-3-phenylpropyl)-$N^6$-trifluoroacetyl-L-lysine. The crystallization velocity is generally not more than about 50% of the whole crystallization amount per hour, preferably not more than about 25% of the whole crystallization amount per hour.

In case of cooling crystallization, the cooling rate is generally not more than about 40° C./hour, preferably not more than about 10° C./hour, more preferably not more than about 5° C./hour. Also, since rapid crystallization by breakage of high supersaturation formed is unfavorable from the viewpoint of quality, it is also preferable to cause nucleation smoothly by adding seed crystals as occasion demands.

The crystallization concentration at the end of crystallization is not particularly limited. Although it varies depending on the kind and ratio of the solvent used, the concentration in the weight of $N^2$-(1(S)-ethoxycarbonyl-3-phenylpropyl)-$N^6$-trifluoroacetyl-L-lysine to the volume of solvent is generally from about 1 to about 50 w/v %, preferably from about 3 to about 40 w/v %, more preferably from 5 to 30 w/v %.

The purification process of the present invention exhibits a high impurity removal effect and can effectively remove the diastereomer ($N^2$-(1(R)-ethoxycarbonyl-3-phenylpropyl)-$N^6$-trifluoroacetyl-L-lysine), the cyclohexyl derivative ($N^2$-(1(S)-ethoxycarbonyl-3-cyclohexylpropyl)-$N^6$-trifluoroacetyl-L-lysine), the carboxyl derivative ($N^2$-(1(S)-carboxy-3-phenylpropyl)-$N^6$-trifluoroacetyl-L-lysine), the ester derivative ($N^2$-(1(S)-ethoxycarbonyl-3-phenylpropyl)-$N^6$-trifluoroacetyl-L-lysine ester), and ethyl phenylbutyrate. In particular, the process exhibits an excellent effect of removing the cyclohexyl derivative which is very hard to be removed.

In order to promote the removal of impurities, it is also effective to previously treat a crystallizing solution with an adsorbent, preferably activated carbon, and then subjecting the solution to crystallization.

The crystals of $N^2$-(1(S)-ethoxycarbonyl-3-phenylpropyl)-$N^6$-trifluoroacetyl-L-lysine obtained by the purification process of the present invention can be obtained as a wet product by usual operation of solid-liquid separation and washing of a cake (centrifugation, pressure filtration, filtration under reduced pressure, etc.), or can be obtained as a dry product by usual drying operation (e.g., flash drying, drying under reduced pressure, vacuum drying and the like). The solid-liquid separation can be performed under cooling at a temperature of not higher than about 20° C., preferably at a temperature of 0 to 10° C., to maximize the yield.

The purification process of the present invention can be suitably utilized, for example, as an isolation process or a recrystallization process for obtaining $N^2$-(1(S)-ethoxycarbonyl-3-phenylpropyl)-$N^6$-trifluoroacetyl-L-lysine synthesized by known processes as mentioned above, especially $N^2$-(1(S)-ethoxycarbonyl-3-phenylpropyl)-$N^6$-trifluoroacetyl-L-lysine synthesized by the above-mentioned process (a) using a Michael addition reaction, in the form of crystals, though the application is not limited thereto.

According to the purification process of the present invention, crystals with high quality and good physical properties can be obtained in a high yield, as mentioned above.

Besides, it has been found that in case that crystallization of $N^2$-(1(S)-ethoxycarbonyl-3-phenylpropyl)-$N^6$-trifluoroacetyl-L-lysine is conducted from a water-soluble non-protic solvent/water mixed solvent according to the purification process of the present invention, plural polymorphs and crystal habits are present in the obtained crystals. All crystals with these polymorphs or crystal habit show a very good filterability and a good purity and are suitable for the production on an industrial scale. Further improvement in quality and/or yield can be achieved by performing polymorph control and/or crystal habit control as mentioned below.

In the crystallization from a water-soluble non-protic organic solvent/water mixed solvent, $N^2$-(1(S)-ethoxycarbonyl-3-phenylpropyl)-$N^6$-trifluoroacetyl-L-lysine is obtained as crystals of the hydrate. Investigation of the amount of crystal water present inside the crystals by a method, wherein the solvent attaching to the crystals was first removed by drying or washing and then the amount of crystal water was determined by vacuum drying to remove the crystal water or by a Karl Fischer's method, revealed that the crystal water is present in an amount of 100 to 130% by mole based on $N^2$-(1(S)-ethoxycarbonyl-3-phenylpropyl)-$N^6$-trifluoroacetyl-L-lysine (dry matter). From this result, it is conjectured that the hydrate crystals are probably monohydrate.

Figure 4:
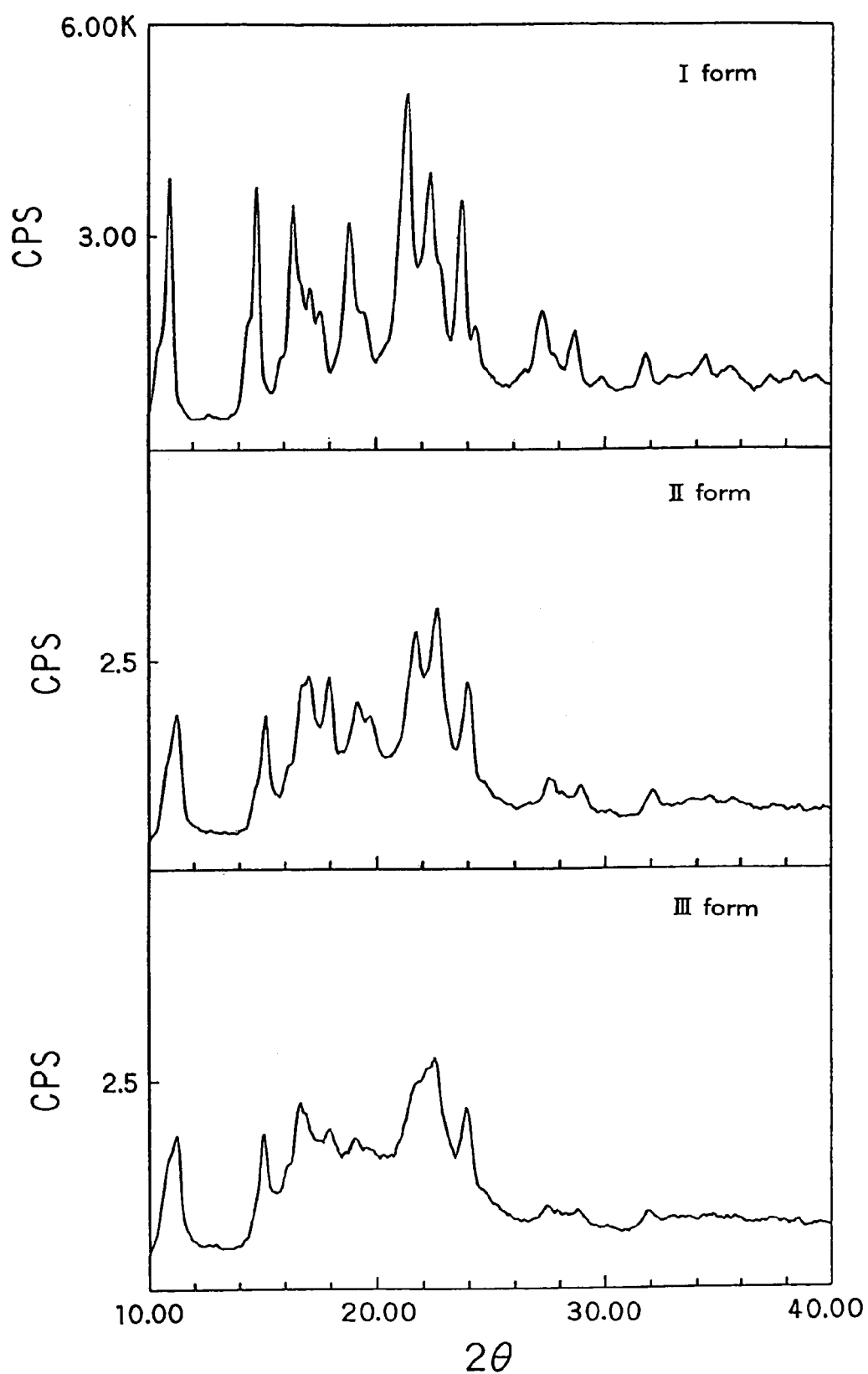
FIG. 4 shows powder X-ray diffraction patterns of polymorphs (I form, II form and III form) of $N^2$-(1(S)-ethoxycarbonyl-3-phenyl-propyl)-$N^6$-trifluoroacetyl-L-lysine.

The hydrate crystals have three polymorphs (I form, II form and III form). It is not easy to identify these polymorphs by powder X-ray diffraction pattern of hydrate crystals, but it is possible to identify them by powder X-ray diffraction pattern of crystals obtained by drying to remove the crystal water, provided that since solid state transformation may further proceed by excessive thermal history at the time of the drying, it is needed for the identification to suppress the transformation by conducting the drying at a relatively low temperature (e.g., vacuum drying at 40° C. and not higher than 5 mmHg). The drying is conducted up to constant weight. In FIG. 4 are shown powder X-ray diffraction patterns of crystals obtained by drying respective polymorphs of the hydrate crystals of $N^2$-(1(S)-ethoxycarbonyl-3-phenyl-propyl)-$N^6$-trifluoroacetyl-L-lysine under conditions that further transformation does not proceed.

Figure 6:
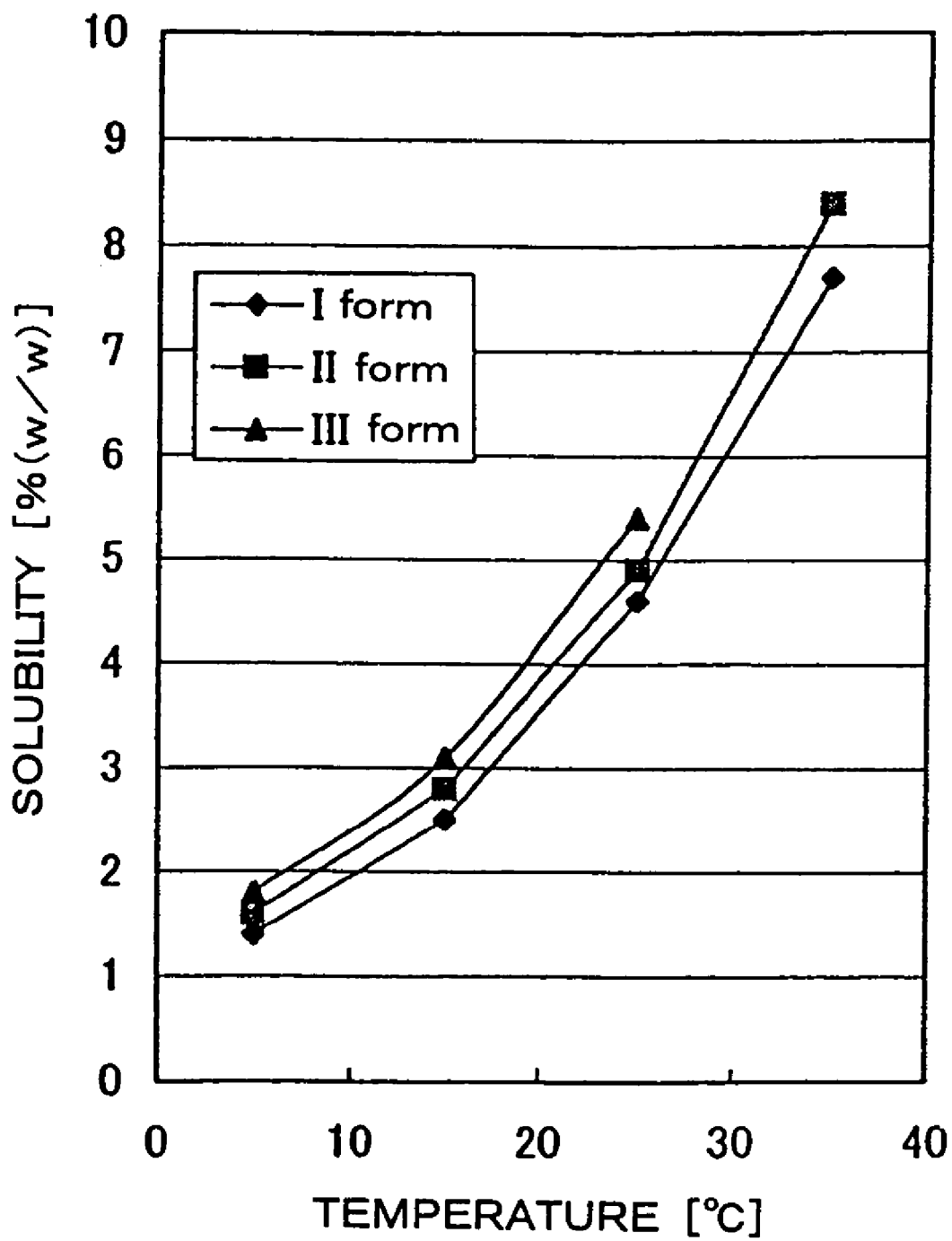
FIG. 6 is a graph showing the solubility (% by weight) of each of polymorphs (I form, II form and III form) of $N^2$-(1(S)-ethoxycarbonyl-3-phenylpropyl)-$N^6$-trifluoroacetyl-L-lysine in a water/acetonitrile mixed solvent (water/acetonitrile volume ratio 0.25)

The solubility of each of the polymorphs is shown in FIG. 6. I form is a stable form having the lowest solubility. The solubilities of these polymorphs in a water/acetonitrile mixed solvent (water/acetonitrile volume ratio 0.25) at 15° C. under ordinary pressure are about 2.5% by weight for I form, about 2.7% by weight for II form and about 3.1% by weight for III form. In a practical crystallization system for the purification of $N^2$-(1(S)-ethoxycarbonyl-3-phenyl-propyl)-$N^6$-trifluoroacetyl-L-lysine, the difference in solubility between the respective polymorphs becomes larger by influence of coexisting impurities, so a difference in yield of about 3% or more may occur between the II form crystals and the III form crystals and a difference in yield of about 5% or more may occur between the I form crystals and the III form crystals. Therefore, if the polymorphism can be controlled in the crystallization to selectively crystallize out the I form or the II form, preferably only the I form, it is very advantageous in the yield.

Figure 5A:
FIG. 5(a) and FIG. 5(b) are SEM photographs of respective crystal habits (α crystals and β crystals) of $N^2$-(1(S)-ethoxycarbonyl-3-phenylpropyl)-$N^6$-trifluoroacetyl-L-lysine.
Figure 5B:
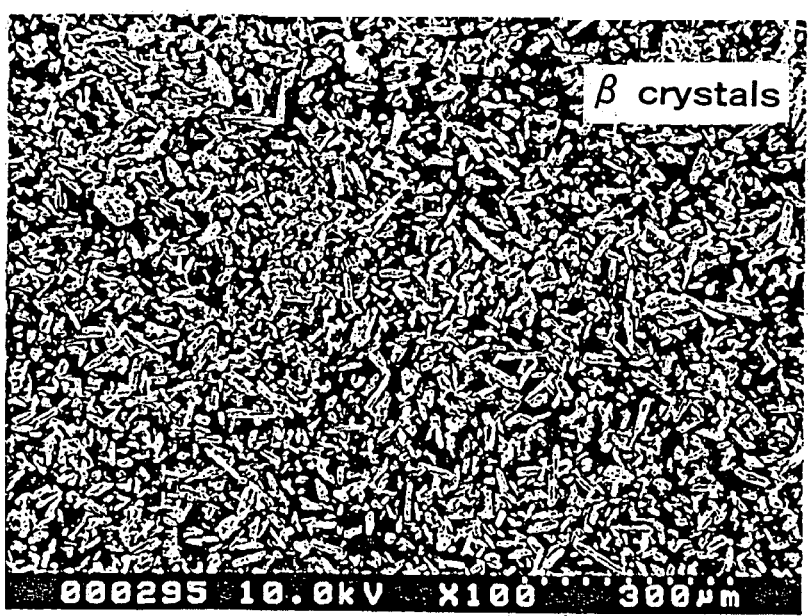

Besides the polymorphism, two kinds of crystal habit (α form and β form) are present in the crystals of $N^2$-(1(S)-ethoxycarbonyl-3-phenyl-propyl)-$N^6$-trifluoroacetyl-L-lysine obtained by the purification process of the present invention. The crystal habit can be relatively easily identified by the appearance of the hydrate crystals or their dried crystals. In FIG. 5 are shown SEM photographs of crystals having each crystal habit.

Of two kinds of crystal habit, the α crystals are mainly crystals having a minor axis of not more than about 30 μm and a major axis of about 200 μm, and the β crystals are mainly crystals having a minor axis of not more than about 10 μm and a major axis of not more than about 50 μm. Although these crystal sizes may vary depending on agitating strength and the like, the α crystals have a larger size than the β crystals. Besides the difference in crystal size, between these crystal forms there is also found a difference in quality such that when the β crystals crystallize out, the content of the diastereomer contaminant decreases. Therefore, if the β crystals can be selectively crystallized, it is advantageous in quality.

According to inventors' preliminary investigation, the above-mentioned polymorphism and crystal habit phenomenon do not always show a good reproducibility, and the same polymorphs and crystal habit were not always obtained even if a slurry of crystals which have given some specific polymorph and crystal habit is dissolved under heating and crystallized again. Also, as a matter of deep interest, it appeared from the results of powder X-ray diffraction patterns and microscopic observation that the obtained crystals were relatively pure crystals from the viewpoints of polymorph and crystal habit.

Firstly, polymorphism control is explained below. It has been found, as a result of present inventors' investigation, that good results are obtained when the amount of the carboxyl derivative coexisting in the crystallization system is small. That is to say, there was observed a tendency that I form or II form is easy to be obtained if crystallization is performed using $N^2$-(1(S)-ethoxycarbonyl-3-phenyl-propyl)-$N^6$-trifluoroacetyl-L-lysine having a carboxyl derivative content of not more than 6% by weight, and I form is easy to be obtained if crystallization is performed using $N^2$-(1(S)-ethoxycarbonyl-3-phenyl-propyl)-$N^6$-trifluoroacetyl-L-lysine having a carboxyl derivative content of not more than 2% by weight. Further, a more evident correlation was recognized between each polymorph and the content of carboxyl derivative contaminant in the obtained crystals, and all of the obtained crystals were I form when the content of that contaminant was not more than 0.5% by weight and were II form when the content of that contaminant was within the range of 0.5 to 1% by weight. From these results, as one of methods for improving the yield can be adopted such a manner as suppressing inclusion of the carboxyl derivative into the obtained crystals by using $N^2$-(1(S)-ethoxycarbonyl-3-phenylpropyl)-$N^6$-trifluoroacetyl-L-lysine having a low carboxyl derivative content as a raw material, thereby obtaining a preferable polymorph (improving the yield).

However, it would be important and significant, from a practical point of view, to establish a more sure and direct method for controlling polymorphism which is not affected by the content of carboxyl derivative in the raw material or does not depend on only the content of carboxyl derivative in the raw material.

As a result of making a study for establishing a more excellent polymorphism controlling method, it has been found that the amount of the carboxyl derivative coexisting in the crystallization system has a close relation to the pH of the crystallization system, and further that the polymorphism mentioned above is also influenced by the crystallizing pH and the I form is selectively obtained at a pH of not less than 4.5, provided that at a pH of less than 4.5 the type of the obtained polymorph tends to depend on the amount of the carboxyl derivative included in the crystals and all polymorphs are found to crystallize out.

It has been found from the above results that the above-mentioned polymorphism occurs from intertwining two factors, the crystallizing pH and the content of carboxyl derivative contaminant, and the pH adjustment (pH 4.5 or higher) of the crystallizing liquid is very useful for selectively obtaining the I form. The I form can be selectively obtained (high yield can be stably achieved) by carrying out the crystallization with adjusting the pH to and/or maintaining the pH at not less than 4.5, preferably 4.5 to 5.5, more preferably 4.6 to 5.2, even in the case where $N^2$-(1(S)-ethoxycarbonyl-3-phenylpropyl)-$N^6$-trifluoro-acetyl-L-lysine having a high carboxyl derivative content is used.

Crystal habit control will be then explained. As a result of present inventors' investigation, it has been found that crystal habit modification based on action of an external force capable of imparting movement, sway or vibration to the crystallization system is effective for selectively obtaining the β crystals. As the external force, there can be mentioned vibration, ultrasonic wave and the like, and external force can be acted on by a method such as conducting agitation with agitating axis being slanted to impart a strong vibration, or using a ultrasonic generator. By such a method, crystals (β crystals) of $N^2$-(1(S)-ethoxycarbonyl-3-phenylpropyl)-$N^6$-trifluoroacetyl-L-lysine of high quality can be selectively obtained.

Further, crystals of $N^2$-(1(S)-ethoxycarbonyl-3-phenylpropyl)-$N^6$-trifluoroacetyl-L-lysine of higher quality can be obtained in a high yield by combining the polymorph control and the crystal habit control.

The present invention is more specifically explained by means of the following examples in which % is by weight unless otherwise noted. It is to be understood that the present invention is not limited to these examples.

PREPARATION EXAMPLE

Preparation of $N^2$-(1-ethoxycarbonyl-3-phenylpropyl)-$N^6$-trifluoroacetyl-L-lysine To 100 ml of ethanol were added 9.69 g of $N^6$-trifluoroacetyl-L-lysine and 8.16 g of trans-ethyl β-benzoylacrylate. Thereto was added 40 ml of 1N aqueous solution of lithium hydroxide over about 2 hours with stirring, while maintaining the temperature at about −5° C., and the stirring was further continued for 30 minutes. The reaction was terminated by adding 10 ml of concentrated hydrochloric acid thereto. To the reaction mixture were added 130 ml of ethanol and 5 g of 10% palladium-carbon, and a reduction reaction was carried out at about 40° C. under ordinary pressure. After the reaction, the catalyst was removed by suction filtration. The obtained ethanol solution was adjusted to about pH 4 with sodium hydroxide, added with water and concentrated under reduced pressure to distil away ethanol so as to replace the solvent with water. The resulting crystals were filtered with suction and dried under vacuum to give 33 g of $N^2$-(1-ethoxycarbonyl-3-phenylpropyl)-$N^6$-trifluoroacetyl-L-lysine (1S/1R ratio =80/20).

EXAMPLE 1

Crude $N^2$-(1(S)-ethoxycarbonyl-3-phenylpropyl)-$N^6$-trifluoro-acetyl-L-lysine (having a purity of 79% and containing as impurities 15% of $N^2$-(1(R)-ethoxycarbonyl-3-phenylpropyl)-$N^6$-trifluoroacetyl-L-lysine, 0.43% of $N^2$-(1(S)-ethoxycarbonyl-3-cyclohexylpropyl)-$N^6$-trifluoroacetyl-L-lysine and the like) was dissolved in an amount corresponding to 2 g of pure one in 10 ml of acetonitrile at a temperature of 50 to 60° C. After filtering the hot solution with suction to remove insoluble matter, the crystallization was carried out by cooling the filtrate to 20° C. at a rate of 10° C./hour with stirring. The resulting crystals were filtered off and washed with cold acetonitrile. The filterability was very good. The crystals were vacuum-dried at a temperature of 20 to 40° C. to give 1.6 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 97%, and the content of $N^2$-(1(R)-ethoxycarbonyl-3-phenylpropyl)-$N^6$-trifluoroacetyl-L-lysine was 1.9% and the content of $N^2$-(1(S)-ethoxycarbonyl-3-cyclohexylpropyl)-$N^6$-trifluoroacetyl-L-lysine was 0.20%.

EXAMPLE 2

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 15 ml of a water/acetonitrile mixed solvent (water/acetonitrile volume ratio 0.25) at an elevated temperature.

After filtering the hot solution with suction to remove insoluble matter, the crystallization was carried out by cooling the filtrate to 20° C. with stirring. The resulting crystals were filtered off and washed with a water/cold acetonitrile mixed solvent (volume ratio 0.25). The filterability was very good. The crystals were vacuum-dried at a temperature of 20 to 40° C. to give 1.3 g of dry crystals (crystals of non-hydrate) of $N^2$-(1(1(S)-ethoxycarbonyl-3-phenylpropyl)-$N^6$-trifluoro-acetyl-L-lysine. The obtained crystals had a purity of 96%, and the content of $N^2$-(1(R)-ethoxycarbonyl-3-phenylpropyl)-$N^6$-trifluoroacetyl-L-lysine was 1.2% and the content of $N^2$-(1(S)-ethoxycarbonyl-3-cyclohexylpropyl)-$N^6$-trifluoroacetyl-L-lysine was 0.16%.

EXAMPLE 3

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 10 ml of a water/acetonitrile mixed solvent (water/acetonitrile volume ratio 0.25) at an elevated temperature. After filtering the hot solution with suction to remove insoluble matter, the crystallization was carried out by cooling the filtrate to 20° C. with stirring. The resulting crystals were filtered off and washed with a water/cold acetonitrile mixed solvent (volume ratio 0.25). The filterability was very good. The crystals were vacuum-dried at a temperature of 20 to 40° C. to give 1.7 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 97%, and the content of $N^2$-(1(R)-ethoxycarbonyl-3-phenylpropyl)-$N^6$-trifluoroacetyl-L-lysine was 1.0% and the content of $N^2$-(1(S)-ethoxycarbonyl-3-cyclohexylpropyl)-$N^6$-trifluoroacetyl-L-lysine was 0.18%.

EXAMPLE 4

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 27 ml of a water/acetone mixed solvent (water/acetone volume ratio 1) at an elevated temperature. After filtering the hot solution with suction to remove insoluble matter, the crystallization was carried out by cooling the filtrate to 20° C. with stirring. The resulting crystals were filtered off and washed with a water/cold acetone mixed solvent (volume ratio 1). The filterability was acceptable. The crystals were vacuum-dried at a temperature of 20 to 30° C. to give 1.7 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 98%, and the content of $N^2$-(1(R)-ethoxycarbonyl-3-phenylpropyl)-$N^6$-trifluoroacetyl-L-lysine was 1.5% and the content of $N^2$-(1(S)-ethoxycarbonyl-3-cyclohexylpropyl)-$N^6$-trifluoroacetyl-L-lysine was 0.22%.

EXAMPLE 5

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 25 ml of a water/tetrahydrofuran mixed solvent (water/tetrahydrofuran volume ratio 1) at an elevated temperature. After filtering the hot solution with suction to remove insoluble matter, the crystallization was carried out by cooling the filtrate to 20° C. with stirring. The resulting crystals were filtered off and washed with a water/tetrahydrofuran mixed solvent (volume ratio 1). The filterability was very good. The crystals were vacuum-dried at a temperature of 20 to 40° C. to give 1.5 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 94%, and the content of $N^2$-(1(R)-ethoxycarbonyl-3-phenylpropyl)-$N^6$-trifluoroacetyl-L-lysine was 3.9% and the content of $N^2$-(1(S)-ethoxycarbonyl-3-cyclohexylpropyl)-$N^6$-trifluoroacetyl-L-lysine was 0.30%.

COMPARATIVE EXAMPLE 1

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 30 ml of a water/methanol mixed solvent (water/methanol volume ratio 1) at an elevated temperature. After filtering the hot solution with suction to remove insoluble matter, the crystallization was carried out by cooling the filtrate to 20° C. with stirring. The resulting crystals were filtered off and washed with a water/cold methanol mixed solvent (volume ratio 1). The filterability was very bad. The crystals were vacuum-dried at a temperature of 20 to 40° C. to give 1.6 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 97%, and the content of $N^2$-(1(R)-ethoxycarbonyl-3-phenylpropyl)-$N^6$-trifluoroacetyl-L-lysine was 1.5% and the content of $N^2$-(1(S)-ethoxycarbonyl-3-cyclohexylpropyl)-$N^6$-trifluoroacetyl-L-lysine was 0.27%.

COMPARATIVE EXAMPLE 2

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 20 ml of a water/ethanol mixed solvent (water/ethanol volume ratio 0.43) at an elevated temperature. After filtering the hot solution with suction to remove insoluble matter, the crystallization was carried out by cooling the filtrate to 20° C. with stirring. The resulting crystals were filtered off and washed with a water/cold ethanol mixed solvent (volume ratio 0.43). The filterability was very bad. The crystals were vacuum-dried at a temperature of 20 to 40° C. to give 1.6 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 97%, and the content of $N^2$-(1(R)-ethoxycarbonyl-3-phenylpropyl)-$N^6$-trifluoroacetyl-L-lysine was 2.0% and the content of $N^2$-(1(S)-ethoxycarbonyl-3-cyclohexylpropyl)-$N^6$-trifluoroacetyl-L-lysine was 0.18%.

COMPARATIVE EXAMPLE 3

The same crude $N^2$-(1(S)-ethoxycarbonyl-3-phenylpropyl)-$N^6$-trifluoroacetyl-L-lysine as that used in Example 1 was dissolved in an amount corresponding to 2 g of pure one in 18 ml of a water/isopropanol mixed solvent (water/isopropanol volume ratio 0.25) at an elevated temperature. After filtering the hot solution with suction to remove insoluble matter, the crystallization was carried out by cooling the filtrate to 20° C. with stirring. The resulting crystals were filtered off and washed with a water/cold isopropanol mixed solvent (volume ratio 0.25). The filterability was very bad. The crystals were vacuum-dried at a temperature of 20 to 40° C. to give 1.3 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 97%, and the content of $N^2$-(1(R)-ethoxycarbonyl-3-phenylpropyl)-$N^6$-trifluoroacetyl-L-lysine was 1.0% and the content of $N^2$-(1(S)-ethoxycarbonyl-3-cyclohexylpropyl)-$N^6$-trifluoroacetyl-L-lysine was 0.20%.

EXAMPLE 6

The same crude $N^2$-(1(S)-ethoxycarbonyl-3-phenylpropyl)-$N^6$-trifluoroacetyl-L-lysine as that used in Example 1, the amount of which corresponded to 2 g of pure one, was added to 25 ml of a water/acetonitrile mixed solvent (water/acetonitrile volume ratio 0.25), and dissolved at 20° C. by adding concentrated hydrochloric acid thereto. The resulting solution was adjusted to pH 4.2 by adding a 30% aqueous solution of sodium hydroxide thereto with stirring to perform neutralizing crystallization at 20° C. The resulting crystals were filtered off and washed with a water/cold acetonitrile mixed solvent (volume ratio 0.25). The filterability was good. The crystals were vacuum-dried at a temperature of 20 to 40° C. to give 1.0 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 94%, and the content of $N^2$-(1(R)-ethoxycarbonyl-3-phenylpropyl)-$N^6$-trifluoroacetyl-L-lysine was 1.0% and the content of $N^2$-(1(S)-ethoxycarbonyl-3-cyclohexylpropyl)-$N^6$-trifluoroacetyl-L-lysine was 0.15%.

EXAMPLE 7

The same crude $N^2$-(1(S)-ethoxycarbonyl-3-phenylpropyl)-$N^6$-trifluoroacetyl-L-lysine as that used in Example 1, the amount of which corresponded to 2 g of pure one, was added to 25 ml of a water/acetonitrile mixed solvent (water/acetonitrile volume ratio 0.25), and dissolved at 20° C. by adding a 30% aqueous solution of sodium hydroxide thereto. The resulting solution was adjusted to pH 4.2 by adding concentrated hydrochloric acid thereto with stirring to perform neutralizing crystallization at 20° C. The resulting crystals were filtered off and washed with a water/cold acetonitrile mixed solvent (volume ratio 0.25). The filterability was good. The crystals were vacuum-dried at a temperature of 20 to 40° C. to give 1.0 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 95%, and the content of $N^2$-(1(R)-ethoxycarbonyl-3-phenylpropyl)-$N^6$-trifluoroacetyl-L-lysine was 2.0% and the content of $N^2$-(1(S)-ethoxycarbonyl-3-cyclohexylpropyl)-$N^6$-trifluoroacetyl-L-lysine was 0.17%.

EXAMPLE 8

The same crude $N^2$-(1(S)-ethoxycarbonyl-3-phenylpropyl)-$N^6$-trifluoroacetyl-L-lysine as that used in Example 1 was dissolved in an amount corresponding to 15 g of pure one in 100 ml of a water/acetonitrile mixed solvent (water/acetonitrile volume ratio 1) at a temperature of 50 to 60° C. After filtering the hot solution with suction to remove insoluble matter, the crystallization was carried out by cooling the filtrate to 20° C. with stirring. The resulting crystals were filtered off by a Nutsche funnel having an inner diameter of 9 cm. The filtering time was 13 seconds. The filter cake was sufficiently pressed by a spatula, and the filtrate was passed therethrough. The passing time was 76 seconds. The filter cake was washed with 23 ml of a water/acetonitrile mixed solvent (volume ratio 1) (the volume of which corresponded to 1.2 times the weight of crude $N^2$-(1-ethoxycarbonyl-3-phenylpropyl)-$N^6$-trifluoroacetyl-L-lysine used for the crystallization). The time needed for the washing was 29 seconds. The cake was vacuum-dried at a temperature of 20 to 40° C. to give 13.0 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 98%, and the content of $N^2$-(1(R)-ethoxycarbonyl-3-phenylpropyl)-$N^6$-trifluoroacetyl-L-lysine was 1.3% and the content of $N^2$-(1(S)-ethoxycarbonyl-3-cyclohexylpropyl)-$N^6$-trifluoroacetyl-L-lysine was 0.20%.

EXAMPLE 9

The same crude $N^2$-(1(S)-ethoxycarbonyl-3-phenylpropyl)-$N^6$-trifluoroacetyl-L-lysine as that used in Example 1 was dissolved in an amount corresponding to 20 g of pure one in 100 ml of a water/acetonitrile mixed solvent (water/acetonitrile volume ratio 0.33) at an elevated temperature. After filtering the hot solution with suction to remove insoluble matter, the crystallization was carried out by cooling the filtrate to 20° C. with stirring. The resulting crystals were filtered off by a Nutsche funnel having an inner diameter of 9 cm. The filtering time was 10 seconds. The filter cake was sufficiently pressed by a spatula, and the filtrate was passed therethrough. The passing time was 50 seconds. The filter cake was washed with 30 ml of a water/acetonitrile mixed solvent (volume ratio 0.33) (the volume of which corresponded to 1.2 times the weight of crude $N^2$-(1-ethoxycarbonyl-3-phenylpropyl)-$N^6$-trifluoroacetyl-L-lysine used for the crystallization). The time needed for the washing was 29 seconds. The cake was vacuum-dried at a temperature of 20 to 40° C. to give 17.0 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 97%, and the content of $N^2$-(1(R)-ethoxycarbonyl-3-phenylpropyl)-$N^6$-trifluoroacetyl-L-lysine was 1.0% and the content of $N^2$-(1(S)-ethoxycarbonyl-3-cyclohexylpropyl)-$N^6$-trifluoroacetyl-L-lysine was 0.17%.

EXAMPLE 10

The same crude $N^2$-(1(S)-ethoxycarbonyl-3-phenylpropyl)-$N^6$-trifluoroacetyl-L-lysine as that used in Example 1 was dissolved in an amount corresponding to 15 g of pure one in 100 ml of a water/acetonitrile mixed solvent (water/acetonitrile volume ratio 0.11) at an elevated temperature. After filtering the hot solution with suction to remove insoluble matter, the crystallization was carried out by cooling the filtrate to 20° C. with stirring. The resulting crystals were filtered off by a Nutsche funnel having an inner diameter of 9 cm. The filtering time was 13 seconds. The filter cake was sufficiently pressed by a spatula, and the filtrate was passed therethrough. The passing time was 50 seconds. The filter cake was washed with 23 ml of a water/acetonitrile mixed solvent (volume ratio 0.11) (the volume of which corresponded to 1.2 times the weight of crude $N^2$-(1-ethoxycarbonyl-3-phenylpropyl)-$N^6$-trifluoroacetyl-L-lysine used for the crystallization). The time needed for the washing was 29 seconds. The cake was vacuum-dried at a temperature of 20 to 40° C. to give 13.3 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 96%, and the content of $N^2$-(1(R)-ethoxycarbonyl-3-phenylpropyl)-$N^6$-trifluoroacetyl-L-lysine was 1.2% and the content of $N^2$-(1(S)-ethoxycarbonyl-3-cyclohexylpropyl)-$N^6$-trifluoroacetyl-L-lysine was 0.22%.

EXAMPLE 11

The same crude $N^2$-(1(S)-ethoxycarbonyl-3-phenylpropyl)-$N^6$-trifluoroacetyl-L-lysine as that used in Example 1 was dissolved in an amount corresponding to 15 g of pure one in 100 ml of acetonitrile at an elevated temperature. After filtering the hot solution with suction to remove insoluble matter, the crystallization was carried out by cooling the filtrate to 20° C. with stirring. The resulting crystals were filtered off by a Nutsche funnel having an inner diameter of 9 cm. The filtering time was 15 seconds. The filter cake was sufficiently pressed by a spatula, and the filtrate was passed therethrough. The passing time was 90 seconds. The filter cake was washed with 23 ml of acetonitrile (the volume of which corresponded to 1.2 times the weight of crude $N^2$-(1-ethoxycarbonyl-3-phenylpropyl)-$N^6$-trifluoroacetyl-L-lysine used for the crystallization). The time needed for the washing was 40 seconds. The cake was vacuum-dried at a temperature of 20 to 40° C. to give 11.9 g of dry crystals (crystals of non-hydrate) of $N^2$-(1(S)-ethoxycarbonyl-3-phenylpropyl)-$N^6$-trifluoroacetyl-L-lysine. The obtained crystals had a purity of 96%, and the content of $N^2$-(1(R)-ethoxycarbonyl-3-phenylpropyl)-$N^6$-trifluoroacetyl-L-lysine was 2.2% and the content of $N^2$-(1(S)-ethoxycarbonyl-3-cyclohexylpropyl)-$N^6$-trifluoroacetyl-L-lysine was 0.21%.

COMPARATIVE EXAMPLE 4

The same crude $N^2$-(1(S)-ethoxycarbonyl-3-phenylpropyl)-$N^6$-trifluoroacetyl-L-lysine as that used in Example 1 was dissolved in an amount corresponding to 20 g of pure one in 200 ml of a water/ethanol mixed solvent (ethanol/water volume ratio 0.43) at an elevated temperature. After filtering the hot solution with suction to remove insoluble matter, the crystallization was carried out by cooling the filtrate to 20° C. with stirring. The resulting crystals were filtered off by a Nutsche funnel having an inner diameter of 9 cm. The filtering time was 210 seconds. The filter cake was sufficiently pressed by a spatula, and the filtrate was passed therethrough. The passing time was 1,860 seconds. The filter cake was washed with 30 ml of a water/ethanol mixed solvent (volume ratio 0.43) (the volume of which corresponded to 1.2 times the weight of crude $N^2$-(1-ethoxycarbonyl-3-phenylpropyl)-$N^6$-trifluoroacetyl-L-lysine used for the crystallization). The time needed for the washing was 180 seconds. The cake was vacuum-dried at a temperature of 20 to 40° C. to give 17.5 g of dry crystals (crystals of non-hydrate) of $N^2$-(1(S)-ethoxycarbonyl-3-phenylpropyl)-$N^6$-trifluoro-acetyl-L-lysine. The obtained crystals had a purity of 97%, and the content of $N^2$-(1(R)-ethoxycarbonyl-3-phenylpropyl)-$N^6$-trifluoroacetyl-L-lysine was 2.0% and the content of $N^2$-(1(S)-ethoxycarbonyl-3-cyclohexylpropyl)-$N^6$-trifluoroacetyl-L-lysine was 0.18%.

EXAMPLE 12

Crude $N^2$-(1(S)-ethoxycarbonyl-3-phenylpropyl)-$N^6$-trifluoro-acetyl-L-lysine (having a purity of 71% and containing as impurities 15% of $N^2$-(1(R)-ethoxycarbonyl-3-phenylpropyl)-$N^6$-trifluoroacetyl-L-lysine (diastereomer), 0.51% of $N^2$-(1(S)-ethoxycarbonyl-3-cyclohexylpropyl)-$N^6$-trifluoroacetyl-L-lysine (cyclohexyl derivative), 8.4% of $N^2$-(1(S)-carboxy-3-phenylpropyl)-$N^6$-trifluoroacetyl-L-lysine (carboxyl derivative), 5.9% of $N^2$-(1(S)-ethoxycarbonyl-3-phenylpropyl)-$N^6$-trifluoroacetyl-L-lysine ethyl ester (ester derivative), 0.4% of ethyl phenylbutyrate and the like) was dissolved in an amount corresponding to 40 g of pure one in 160 ml of a water/acetonitrile mixed solvent (water/acetonitrile volume ratio 0.25) at an elevated temperature. To the solution was added 1.2 g of activated carbon containing 50% of water. After stirring for 15 minutes, activated carbon was removed by suction filtration and washed with a water/acetonitrile mixed solvent (volume ratio 0.25) so as to adjust the concentration of $N^2$-(1(S)-ethoxycarbonyl-3-phenylpropyl)-$N^6$-trifluoroacetyl-L-lysine as a pure compound based on the volume of the solvent to 20 w/v %. This solution was subjected to crystallization in a crystallization vessel equipped with a paddle impeller by cooling the solution from 43° C. to 8° C. over 10 hours under forced flowing condition in terms of 40 W/m³, 300 W/m³, 1,000 W/m³ or 1,800 W/m³ in agitation power per unit volume. The resulting crystals were filtered off, washed with 80 ml of a water/cold acetonitrile mixed solvent (volume ratio 0.25) and dried under vacuum at a temperature of 20 to 40° C. There was observed a tendency that the quality of the obtained crystals is enhanced as the agitation power increases. With respect to the case where the obtained crystals were α crystals, the quality is shown below.

Agitation power 40 W/m³: diastereomer content 1.1%, cyclohexyl derivative content 0.22%, carboxyl derivative content 1.2%, ester derivative content<0.1%, ethyl phenylbutyrate<0.1%

Agitation power 300 W/m³: diastereomer content 0.8%, cyclohexyl derivative content 0.20%, carboxyl derivative content 1.1%, ester derivative content<0.1%, ethyl phenylbutyrate<0.1%

Agitation power 1,000 W/m³: diastereomer content 0.7%, cyclohexyl derivative content 0.19%, carboxyl derivative content 0.8%, ester derivative content<0.1%, ethyl phenylbutyrate<0.1%

Agitation power 1,800 W/m³: diastereomer content 0.6%, cyclohexyl derivative content 0.18%, carboxyl derivative content 0.8%, ester derivative content<0.1%, ethyl phenylbutyrate<0.1%

EXAMPLE 13

Crude $N^2$-(1(S)-ethoxycarbonyl-3-phenylpropyl)-$N^6$-trifluoro-acetyl-L-lysine (having a purity of 73% and containing as impurities 15% of $N^2$-(1(R)-ethoxycarbonyl-3-phenylpropyl)-$N^6$-trifluoroacetyl-L-lysine (diastereomer), 7.8% of $N^2$-(1(S)-carboxy-3-phenylpropyl)-$N^6$-trifluoroacetyl-L-lysine (carboxyl derivative) and the like) was dissolved in an amount corresponding to 40 g of pure one in 160 ml of a water/acetonitrile mixed solvent (water/acetonitrile volume ratio 0.25) at an elevated temperature. To the solution was added 1.2 g of activated carbon containing 50% of water. After stirring for 15 minutes, activated carbon was removed by suction filtration and washed with a water/acetonitrile mixed solvent (volume ratio 0.25) so as to adjust the concentration of $N^2$-(1(S)-ethoxycarbonyl-3-phenylpropyl)-$N^6$-trifluoroacetyl-L-lysine as a pure compound based on the volume of the solvent to 20 w/v %. This solution was subjected to crystallization in a crystallization vessel equipped with a paddle impeller by cooling the solution from 43° C. to 8° C. at a constant rate over 1 hour, 5 hours, 10 hours or 17 hours under a forced flowing condition in terms of 400 W/m$^3$ in agitation power per unit volume. The resulting crystals were filtered off, washed with 80 ml of a water/cold acetonitrile mixed solvent (volume ratio 0.25) and dried under vacuum at a temperature of 20 to 40° C. There was observed a tendency that the smaller the cooling velocity, the higher the quality of the obtained crystals. With respect to the case where the obtained crystals were α crystals of III form, the quality is shown below.

Cooling time 1 hour: diastereomer content 1.5%, carboxyl derivative content 1.6%
Cooling time 5 hours: diastereomer content 1.3%, carboxyl derivative content 1.4%
Cooling time 10 hours: diastereomer content 1.0%, carboxyl derivative content 1.1%
Cooling time 17 hours: diastereomer content 0.9%, carboxyl derivative content 1.2%

EXAMPLE 14

Crude crystals of N$^2$-(1(S)-ethoxycarbonyl-3-phenylpropyl)-N$^6$-trifluoroacetyl-L-lysine were dissolved in an amount of 40 g as pure compound in 200 ml of a water/acetonitrile mixed solvent (water/acetonitrile volume ratio 0.25) at an elevated temperature. Insoluble matter was removed by suction filtration, and the mixed solvent in an amount corresponding to the vaporized solvent was supplemented to adjust the concentration of N$^2$-(1(S)-ethoxycarbonyl-3-phenylpropyl)-N$^6$-trifluoroacetyl-L-lysine as a pure compound based on the volume of the solvent to 20 w/v %. This solution was subjected to crystallization in a crystallization vessel equipped with a paddle impeller by cooling the solution from 43° C. to 8° C. at a constant rate over 10 hours under a forced flowing condition in terms of 400 W/m$^3$ in agitation power per unit volume. With respect to each of the following three kinds of crude crystals of N$^2$-(1(S)-ethoxycarbonyl-3-phenylpropyl)-N$^6$-trifluoro-acetyl-L-lysine having a different quality, the crystallization was repeated 4 times. The quality, polymorphs and crystal habit of the obtained crystals are shown in Table 1. Also, with respect to each of the polymorphs obtained, the quality and crystal habit are put in order and shown in Table 2.

Crude Crystals Used
Crude crystals A: purity 71%, diastereomer content 15%, carboxyl derivative content 8.4%
Crude crystals B: purity 63%, diastereomer content 16%, carboxyl derivative content 5.8%
Crude crystals C: purity 76%, diastereomer content 14%, carboxyl derivative content 1.4%

TABLE 1

| Crude crystals | Octained crystals | | | |
|---|---|---|---|---|
| | Content of carboxyl derivative | Content of diastereomer | Polymorphs | Crystal habit |
| A | 1.40% | 1.29% | III | α |
| | 1.15% | 0.65% | III | α |
| | 0.56% | 0.67% | II | α |
| | 0.39% | 0.44% | I | β |
| B | 1.21% | 0.92% | III | α |
| | 0.76% | 0.75% | II | α |
| | 0.68% | 0.67% | II | β |
| | 0.66% | 0.54% | II | β |
| C | 0.38% | 1.18% | I | α |
| | 0.32% | 1.05% | I | α |

TABLE 1-continued

| Crude crystals | Octained crystals | | | |
|---|---|---|---|---|
| | Content of carboxyl derivative | Content of diastereomer | Polymorphs | Crystal habit |
| | 0.12% | 0.58% | I | β |
| | 0.09% | 0.73% | I | β |

TABLE 2

| Polymorphs | Content of carboxyl derivative | Content of diastereomer | Crystal habit |
|---|---|---|---|
| I | 0.09% | 0.73% | β |
| | 0.12% | 0.58% | β |
| | 0.32% | 1.05% | α |
| | 0.38% | 1.18% | α |
| | 0.39% | 0.44% | β |
| II | 0.56% | 0.67% | α |
| | 0.66% | 0.54% | β |
| | 0.68% | 0.67% | β |
| | 0.76% | 0.75% | α |
| III | 1.15% | 0.65% | α |
| | 1.21% | 0.92% | α |
| | 1.40% | 1.29% | α |

REFERENCE EXAMPLE 1

Powder X-ray diffraction patterns of polymorphs (I form, II form and III form) of N$^2$-(1(S)-ethoxycarbonyl-3-phenylpropyl)-N$^6$-trifluoroacetyl-L-lysine are shown in FIG. 4. Each sample of polymorphs used in the measurement was obtained by drying wet crystals (hydrate crystals) obtained in Example 14 under vacuum (1 to 5 mmHg) at about 40° C. in a compartment tray dryer so as to avoid solid state transformation of the obtained non-hydrate crystals. The powder X-ray diffractiometry is as follows:

Apparatus: X-ray diffractometer RAD-rA (made by Rigaku Denki Kabushiki Kaisha)

Measurement of diffraction angle: 2θ, CuKα radiation

REFERENCE EXAMPLE 2

SEM photographs of respective crystal habits (α crystals and β crystals) of N$^2$-(1(S)-ethoxycarbonyl-3-phenylpropyl)-N$^6$-trifluoro-acetyl-L-lysine are shown in FIG. 5. SEM observation was made under the following conditions.

Apparatus: Scanning electron microscope (Hitachi S4000)

Observation condition: Accelerating voltage 10 kV

Preparation of sample: Pt-Pd vapor deposition

REFERENCE EXAMPLE 3

A 50 ml four-neck flask was charged with 30 ml of a water/acetonitrile mixed solvent (water/acetonitrile volume ratio 0.25). After cooling the solvent to 5° C. with stirring, 5 g of each of polymorphs (I form, II form and II form) of N$^2$-(1(S)-ethoxycarbonyl-3-phenylpropyl)-N$^6$-trifluoro-acetyl-L-lysine was added thereto, and the temperature was elevated to a predetermined temperature at a rate of 10° C./hour. After reaching the predetermined temperature, the solution was maintained at that temperature for about 1 hour. A sample of the resulting saturated solution was taken out, and the concentration (% by weight) of $N^2$-(1(S)-ethoxycarbonyl-3-phenylpropyl)-$N^6$-trifluoroacetyl-L-lysine was measured by HPLC analysis to determine the solubility at that temperature. The results are shown in FIG. 6.

EXAMPLE 15

Crude crystals of $N^2$-(1(S)-ethoxycarbonyl-3-phenylpropyl)-$N^6$-trifluoroacetyl-L-lysine (having a purity of 71% and containing as impurities 15% of $N^2$-(1(R)-ethoxycarbonyl-3-phenylpropyl)-$N^6$-trifluoroacetyl-L-lysine (diastereomer), 8.4% of $N^2$-(1(S)-carboxy-3-phenylpropyl)-$N^6$-trifluoroacetyl-L-lysine (carboxyl derivative) and the like) were dissolved in an amount of 40 g as pure compound in 200 ml of a water/acetonitrile mixed solvent (water/acetonitrile volume ratio 0.25) at an elevated temperature. Insoluble matter was removed by suction filtration, and the mixed solvent in an amount corresponding to the vaporized solvent was supplemented to adjust the concentration of $N^2$-(1(S)-ethoxycarbonyl-3-phenylpropyl)-$N^6$-trifluoroacetyl-L-lysine as a pure compound based on the volume of the solvent to 20 w/v %. This solution was subjected to crystallization in a crystallization vessel equipped with a paddle impeller by cooling the solution from 43° C. to 8° C. at a constant rate over 10 hours under a forced flowing condition in terms of 400 W/m³ in agitation power per unit volume. The resulting crystals were filtered, washed with 80 ml of a water/cold acetonitrile mixed solvent (volume ratio 0.25) and dried under vacuum at a temperature of 20 to 40° C. The yields in the case where I form, II form and III form were crystallized out were 84%, 82% and 79%, respectively.

REFERENCE EXAMPLE 4

Figure 7:
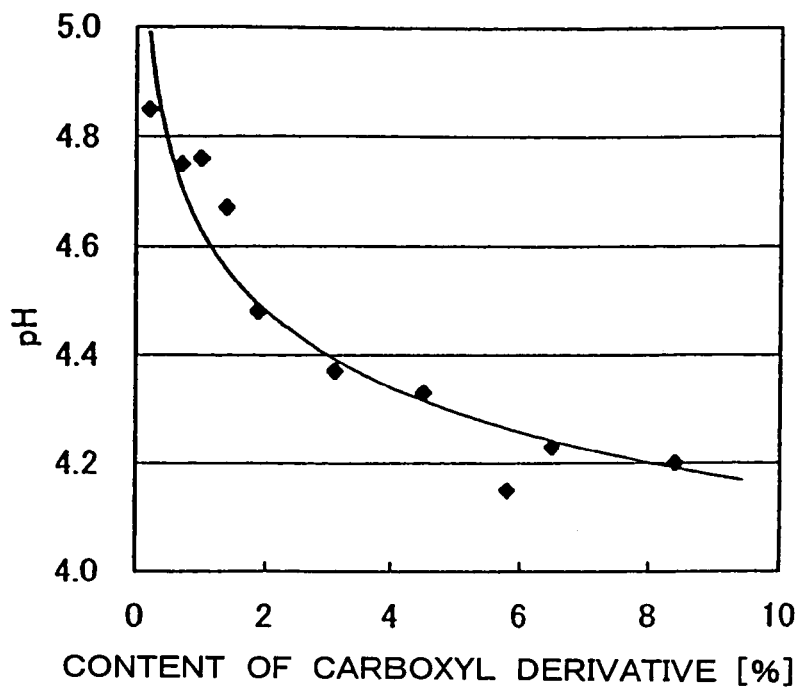
FIG. 7 is a graph showing the relationship between the content of the carboxyl derivative in $N^2$-(1(S)-ethoxycarbonyl-3-phenylpropyl)-$N^6$-trifluoroacetyl-L-lysine to be subjected to crystallization and the pH of a crystallizing solution.

In 20 ml of a water/acetonitrile mixed solvent (water/acetonitrile volume ratio 0.25) was dissolved each of crude crystals of $N^2$-(1(S)-ethoxycarbonyl-3-phenylpropyl)-$N^6$-trifluoroacetyl-L-lysine having different carboxyl derivative contents in an amount of 4 g as pure compound at an elevated temperature. The pH of each solution was measured at an inner temperature of about 40-45° C. and the relationship between the carboxyl derivative content and the pH of the solution was investigated. The results are shown in FIG. 7.

EXAMPLE 16

Crude crystals of $N^2$-(1(S)-ethoxycarbonyl-3-phenylpropyl)-$N^6$-trifluoroacetyl-L-lysine were dissolved in an amount of 40 g as pure compound in 200 ml of a water/acetonitrile mixed solvent (water/acetonitrile volume ratio 0.25) at an elevated temperature. Insoluble matter was removed by suction filtration, and the mixed solvent in an amount corresponding to the vaporized solvent was supplemented to adjust the concentration of $N^2$-(1(S)-ethoxycarbonyl-3-phenylpropyl)-$N^6$-trifluoroacetyl-L-lysine as a pure compound based on the volume of the solvent to 20 w/v %. This solution was adjusted to a predetermined pH at an inner temperature of about 40-45° C. with concentrated sulfuric acid or a 30% aqueous solution of sodium hydroxide, and was then subjected to crystallization in a crystallization vessel equipped with a paddle impeller by cooling the solution from 43° C. to 8° C. at a constant rate over 10 hours under a forced flowing condition in terms of 400 W/m in agitation power per unit volume. In the crystallization, three kinds of crude crystals of $N^2$-(1(S)-ethoxycarbonyl-3-phenylpropyl)-$N^6$-trifluoroacetyl-L-lysine having a different quality were used, and the crystallization was repeated 4 times with respect to each crude crystals. The quality, polymorphs and crystal habit of the obtained crystals are shown in Table 3.

Crude Crystals Used
Crude crystals A: purity 71%, diastereomer content 15%, carboxyl derivative content 8.4%
Crude crystals B: purity 63%, diastereomer content 16%, carboxyl derivative content 5.8%
Crude crystals C: purity 87%, diastereomer content 11%, carboxyl derivative content 0.2%

TABLE 3

| Crude crystals | pH adjusted | Crystals obtained | | |
|---|---|---|---|---|
| | | Content of carboxyl derivative | Polymorphs | Crystal habit |
| A | 5.1 | 0.25% | I | α |
| | 4.7 | 0.29% | I | α |
| | 4.3 | 1.40% | III | α |
| | 4.0 | 0.33% | I | β |
| B | 5.1 | 0.41% | I | α |
| | 4.7 | 0.39% | I | α |
| | 4.3 | 0.33% | II | β |
| | 4.0 | 1.25% | III | α |
| C | 5.1 | <0.1% | I | α |
| | 4.7 | <0.1% | I | β |
| | 4.3 | <0.1% | * | α |
| | 4.0 | <0.1% | II | α |

* It shows an intermediate powder X-ray diffraction pattern between I form and II form.

REFERENCE EXAMPLE 5

The relationship between the crystal size of each of α crystals and β crystals and the content of diastereomer was investigated, since there is a possibility that the difference in quality between the α crystals and the β crystals has no relation to the crystal habit phenomenon, but is only caused by the difference in crystal size. For both samples of α crystals and β crystals, the I form polymorph crystallized from the same crude crystals of $N^2$-(1(S)-ethoxycarbonyl-3-phenylpropyl)-$N^6$-trifluoro-acetyl-L-lysine was used.

Figure 8:
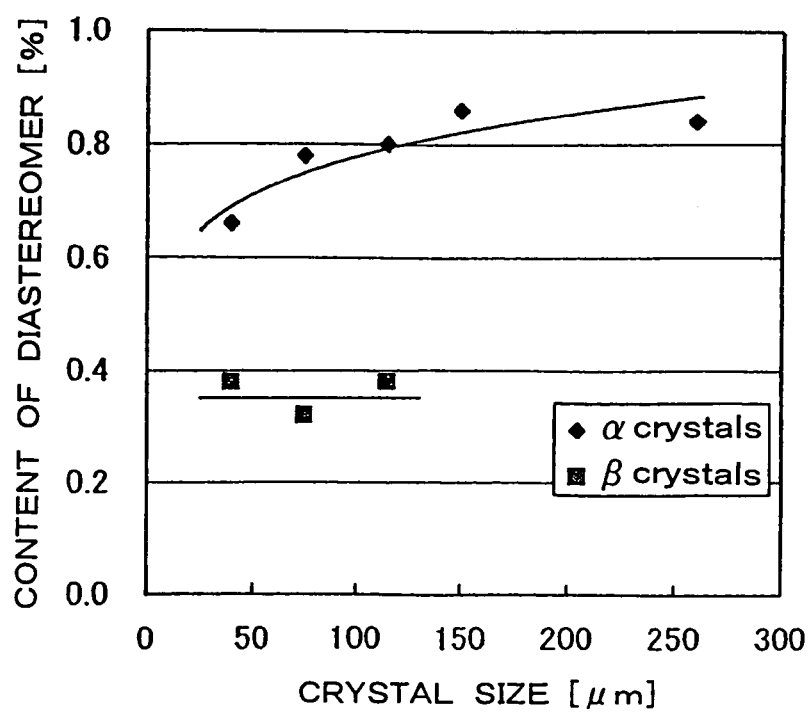
FIG. 8 is a graph showing the relationship between the crystal size of each of crystal habits (α form and β form) of $N^2$-(1(S)-ethoxycarbonyl-3-phenylpropyl)-$N^6$-trifluoroacetyl-L-lysine and the content of the diastereomer included therein.

Using 10 g of the crystal sample of each habit, the crystals were sieved by a wet method to classify with respect to the particle size, and the content of $N^2$-(1(R)-ethoxycarbonyl-3-phenylpropyl)-$N^6$-trifluoroacetyl-L-lysine (diastereomer) in each class of crystals was measured. As a dispersing medium in the wet method was used cyclohexane saturated with $N^2$-(1(S)-ethoxycarbonyl-3-phenylpropyl)-$N^6$-trifluoroacetyl-L-lysine. The results are shown in FIG. 8. In FIG. 8, there is found a clear difference in quality that the β crystals have a smaller content of diastereomer than the α crystals even if they have the same particle size.

EXAMPLE 17

Crude crystals of $N^2$-(1(S)-ethoxycarbonyl-3-phenylpropyl)-$N^6$-trifluoroacetyl-L-lysine (having a purity of 87% and containing as impurities 11% of $N^2$-(1(R)-ethoxycarbonyl-3-phenylpropyl)-$N^6$-trifluoroacetyl-L-lysine (diastereomer), 0.2% of $N^2$-(1(S)-carboxy-3-phenylpropyl)-$N^6$-trifluoroacetyl-L-lysine (carboxyl derivative) and the like) were dissolved in an amount of 40 g as pure compound in 200 ml of a water/acetonitrile mixed solvent (water/acetonitrile volume ratio 0.25) at an elevated temperature. Insoluble matter was removed by suction filtration, and the mixed solvent in an amount corresponding to the vaporized solvent was supplemented to adjust the concentration of $N^2$-(1(S)-ethoxycarbonyl-3-phenylpropyl)-$N^6$-trifluoroacetyl-L-lysine as a pure compound based on the volume of the solvent to 20 w/v %. This solution was subjected to crystallization in a crystallization vessel equipped with a paddle impeller by cooling the solution from 43° C. to 8° C. at a constant rate over 10 hours under a forced flowing condition in terms of 400 W/m³ in agitation power per unit volume. During the crystallization, the axis of agitator was inclined to impart strong vibration to the solution. The above crystallization operation was conducted 4 times, and β crystals were obtained in all of four operations. Thus, the frequency count of obtaining the β crystals was 4/4. The average content of diastereomer was 0.31%.

EXAMPLE 18

Crude crystals of $N^2$-(1(S)-ethoxycarbonyl-3-phenylpropyl)-$N^6$-trifluoroacetyl-L-lysine used in Example 17 (having a purity of 87% and containing as impurities 11% of $N^2$-(1(R)-ethoxycarbonyl-3-phenylpropyl)-$N^6$-trifluoroacetyl-L-lysine (diastereomer), 0.2% of $N^2$-(1(S)-carboxy-3-phenylpropyl)-$N^6$-trifluoroacetyl-L-lysine (carboxyl derivative) and the like) were dissolved in an amount of 40 g as pure compound in 200 ml of a water/acetonitrile mixed solvent (water/acetonitrile volume ratio 0.25) at an elevated temperature. Insoluble matter was removed by suction filtration, and the mixed solvent in an amount corresponding to the vaporized solvent was supplemented to adjust the concentration of $N^2$-(1(S)-ethoxycarbonyl-3-phenylpropyl)-$N^6$-trifluoroacetyl-L-lysine as a pure compound based on the volume of the solvent to 20 w/v %. This solution was subjected to crystallization in a crystallization vessel equipped with a paddle impeller by cooling the solution from 43° C. to 8° C. at a constant rate over 10 hours under a forced flowing condition in terms of 400 W/m³ in agitation power per unit volume. During the crystallization, ultrasonic wave was irradiated to the solution by using the following ultrasonic generator. The above crystallization operation was conducted 4 times, and β crystals were obtained in all of four operations. Thus, the frequency count of obtaining the β crystals was 4/4. The average content of diastereomer was 0.16%.

Specification of Ultrasonic Generator

Name: TOMY Ultrasonic Generator

Model: Model UR-20P

Frequency generated: 28 kHz

Rated output: 20 W

Selling agency: Kabushiki Kaisha Tomy Seiko

EXAMPLE 19

The following operation was conducted for comparison with Examples 17 and 18.

The same crystallization as in Examples 17 and 18 was carried out without imparting a strong vibration by inclination of the axis of agitator and without irradiating ultrasonic wave. The crystallization operation was carried out twice, and α crystals were obtained in both operations. Thus, the frequency count of obtaining α crystals was 2/2. The average content of diastereomer was 0.88%.

EXAMPLE 20

Crude $N^2$-(1(S)-ethoxycarbonyl-3-phenylpropyl)-$N^6$-trifluoro-acetyl-L-lysine (having a purity of 78% and containing as impurities 14% of $N^2$-(1(R)-ethoxycarbonyl-3-phenylpropyl)-$N^6$-trifluoroacetyl-L-lysine (diastereomer), 0.32% of $N^2$-(1(S)-ethoxycarbonyl-3-cyclohexylpropyl)-$N^6$-trifluoroacetyl-L-lysine (cyclohexyl derivative), 1.4% of $N^2$-(1(S)-carboxy-3-phenylpropyl)-$N^6$-trifluoroacetyl-L-lysine (carboxyl derivative), 3.3% of $N^2$-(1(S)-ethoxycarbonyl-3-phenylpropyl)-$N^6$-trifluoroacetyl-L-lysine ethyl ester (ester derivative), 0.4% of ethyl phenylbutyrate and the like) was dissolved in an amount corresponding to 50 g of the pure compound in 250 ml of a water/acetonitrile mixed solvent (water/acetonitrile volume ratio 0.25) at an elevated temperature. The crystallization was carried out by cooling the solution to 20° C. with stirring. The resulting crystals were subjected to centrifugal filtration to evaluate the filterability.

Apparatus: Small-sized centrifugal separator SYK-3800-10A made by Sanyo Rikagakukiki Seisakusho Basket size: inner diameter 100 mm×depth 60 mm TOYO Filter Paper No. 51

Results of Evaluation

1. Slurry charge (2,500 rpm (350G))

Time needed for filtration: 15 seconds (very good filterability)

2. Filtrate recycle charge after attaching cake (2,500 rpm (350G))

Possible treating speed: about 2,000 ml/minute (very good filterability, fast draining)

3. Filtrate recycle recharge (3,500 rpm (700G))

Possible treating speed:>about 2,000 ml/minute (very good filterability, fast draining)

The cake was then washed with 70 ml of a water/acetonitrile mixed solvent (water/acetonitrile volume ratio 0.25). The wet cake showed a dry feeling and could be easily scratched off by a spatula. The wet density of the cake was 0.4 g/ml, and the liquid content (wet basis) was 18%.

The obtained wet crystals were dried under vacuum (at 20 to 40° C.) to give 42 g of dry crystals of $N^2$-(1(S)-ethoxycarbonyl-3-phenylpropyl)-$N^6$-trifluoroacetyl-L-lysine. The obtained crystals had a purity of 98%, and had impurity contents: $N^2$-(1(R)-ethoxycarbonyl-3-phenylpropyl)-$N^6$-trifluoroacetyl-L-lysine (diastereomer) content 0.7%, $N^2$-(1(S)-ethoxycarbonyl-3-cyclohexylpropyl)-$N^6$-trifluoroacetyl-L-lysine (cyclohexyl derivative) content 0.13%, $N^2$-(1(S)-carboxy-3-phenylpropyl)-$N^6$-trifluoroacetyl-L-lysine (carboxyl derivative) content 0.2%, $N^2$-(1(S)-ethoxycarbonyl-3-phenylpropyl)-$N^6$-trifluoroacetyl-L-lysine ethyl ester (ester derivative) content<0.1%, and ethyl phenylbutyrate<0.1%.

COMPARATIVE EXAMPLE 5

The $N^2$-(1(S)-ethoxycarbonyl-3-phenylpropyl)-$N^6$-trifluoro-acetyl-L-lysine containing impurities used in Example 20 was dissolved in an amount corresponding to 50 g of the pure compound in 500 ml of a water/ethanol mixed solvent (water/ethanol volume ratio 0.43) at an elevated temperature. The crystallization was carried out by cooling the solution to 20° C. with stirring. The resulting crystals were subjected to centrifugal filtration to evaluate the filterability in the same manner as in EXAMPLE 20.

Results of Evaluation
1. Slurry charge (2,500 rpm (350G))
   Time needed for filtration: about 40 minutes (much slurry leaks if the charging speed is not controlled.)
2. Filtrate recycle charge after attaching cake (2,500 rpm (350G))
   Possible treating speed: about 15 ml/minute (filterability is very bad, and slurry accumulates in the basket.)
3. Filtrate recycle recharge (3,500 rpm (700G))
   Possible treating speed: about 20 ml/minute (the same as above)

The cake was then washed with 70 ml of a water/ethanol mixed solvent (water/ethanol volume ratio 0.43). The wet cake was cracked and furthermore was very sticky like vanilla ice cream, so it stuck to a spatula and could not be easily scratched off by the spatula. The wet density of the cake was 1.1 g/ml, and the liquid content thereof (wet basis) was 64%.

INDUSTRIAL APPLICABILITY $N^2$-(1(S)-ethoxycarbonyl-3-phenylpropyl)-$N^6$-trifluoroacetyl-L-lysine with a high quality, namely high purity and good crystal physical properties, can be obtained in a high yield and a high productivity by the purification process of the present invention.

The invention claimed is:

1. A process for purifying $N^2$-(1(S)-ethoxycarbonyl-3-phenylpropyl)-$N^6$-trifluoroacetyl-L-lysine of the formula (1):

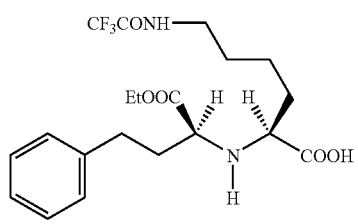

comprising subjecting $N^2$-(1(S)-ethoxycarbonyl-3-phenylpropyl)-$N^6$-trifluoroacetyl-L-lysine contaminated with impurities to crystallization from a water-soluble non-protic organic solvent or a solvent containing a water-soluble non-protic organic solvent, thereby removing the impurities into the mother liquor and giving crystals of $N^2$-(1(S)-ethoxycarbonyl-3-phenylpropyl)-$N^6$-trifluoroacetyl-L-lysine.

2. The process of claim 1, wherein said impurities are at least one compound selected from the group consisting of $N^2$-(1(R)-ethoxycarbonyl-3-phenylpropyl)-$N^6$-trifluoroacetyl-L-lysine of the formula (2):

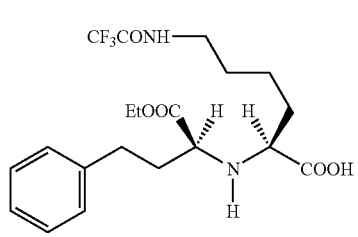

$N^2$-(1(S)-ethoxycarbonyl-3-cyclohexylpropyl)-$N^6$-trifluoroacetyl-L-lysine of the formula (3):

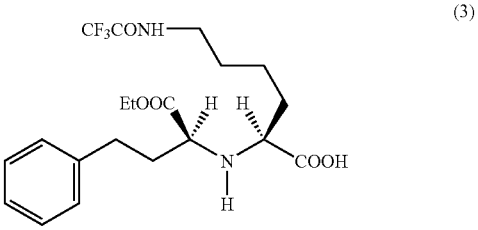

$N^2$-(1(S)-carboxy-3-phenylpropyl)-$N^6$-trifluoroacetyl-L-lysine of the formula (4):

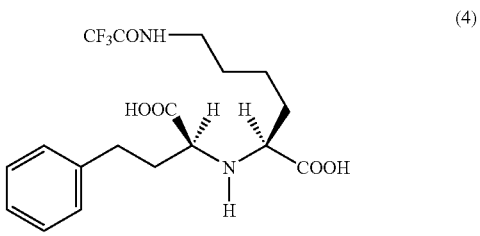

$N^2$-(1(S)-ethoxycarbonyl-3-phenylpropyl)-$N^6$-trifluoroacetyl-L-lysine ester of the formula (5):

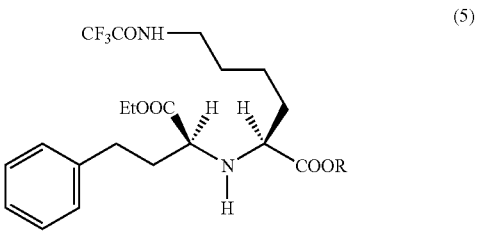

wherein R is an alkyl group, and
ethyl phenylbutyrate.

3. The process of claim 1, wherein said crystallization is carried out under a forced flowing condition.

4. The process of claim 1, wherein said crystallization is carried out at a temperature of not less than 20° C.

5. The process of claim 1, wherein said crystallization is carried out at a crystallization velocity of not more than 50%/hour based on the whole amount of crystals to be crystallized out.

6. The process of claim 1, wherein said crystallization is carried out at a pH of 3 to 6.

7. The process of claim 1, wherein said crystallization is carried out by using at least one of cooling crystallization and concentrating crystallization.

8. The process of claim 1, wherein said crystallization is carried out by cooling crystallization.

9. The process of claim 7 or 8, wherein said cooling crystallization is carried out at a cooling rate of not more than 40° C./hour.

10. The process of claim 1, wherein said solvent used in said crystallization is a mixed solvent of a water-soluble non-protic organic solvent and an auxiliary solvent, and the volume ratio of the auxiliary solvent to the water-soluble non-protic organic solvent is from 0 to 10.

11. The process of claim 1, wherein the crystallizing solution is treated with an adsorbent before carrying out said crystallization.

12. The process of claim 11, wherein said adsorbent is activated carbon.

13. The process of claim 1, wherein seed crystals are added upon carrying out said crystallization.

14. A process for purifying $N^2$-(1(S)-ethoxycarbonyl-3-phenylpropyl)-$N^6$-trifluoroacetyl-L-lysine of the formula (1):

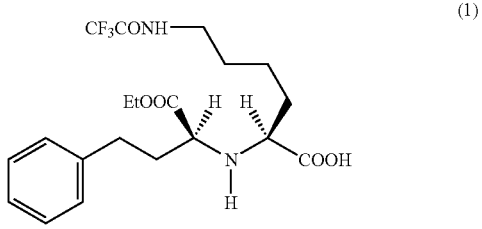

comprising subjecting $N^2$-(1(S)-ethoxycarbonyl-3-phenylpropyl)-$N^6$-trifluoroacetyl-L-lysine contaminated with impurities to crystallization from a water-soluble non-protic organic solvent or a solvent containing a water-soluble non-protic organic solvent, thereby removing the impurities into the mother liquor and giving crystals of N2-(1(S)-ethoxycarbonyl-3-phenylpropyl)-$N^6$-trifluoroacetyl-L-lysine,
wherein said water-soluble non-protic organic solvent is at least one solvent selected from the group consisting of acetonitrile, acetone, methyl ethyl ketone, tetrahydrofuran and dioxane.

15. The process of claim 1, wherein said water-soluble non-protic organic solvent is acetonitrile.

16. The process of claim 1, wherein said solvent containing a water-soluble non-protic organic solvent is a mixed solvent of an auxiliary solvent and a water-soluble non-protic organic solvent in which the auxiliary solvent is water.

17. The process of claim 16, wherein as said $N^2$-(1(S)-ethoxycarbonyl-3-phenylpropyl)-$N^6$-trifluoroacetyl-L-lysine contaminated with impurities and subjected to crystallization containing not more than 6% by weight of $N^2$-(1(S)-carboxy-3-phenylpropyl)-$N^6$-trifluoroacetyl-L-lysine.

18. The process of claim 16, wherein said $N^2$-(1(S)-ethoxycarbonyl-3-phenylpropyl)-$N^6$-trifluoroacetyl-L-lysine contaminated with impurities and subjected to crystallization containing not more than 2% by weight of $N^2$-(1(S)-carboxy-3-phenylpropyl)-$N^6$-trifluoroacetyl-L-lysine.

19. The process of claim 16, wherein said crystallization is carried out after adjusting the crystallizing solution to a pH of not less than 4.5 and/or with maintaining the crystallizing solution at a pH of not less than 4.5.

20. The process of claim 19, wherein the pH of said crystallizing solution is from 4.5 to 5.5.

21. The process of any one of claims 16, wherein said crystallization is carried out under action of external force.

22. The process of claim 21, wherein said external force is selected from the group consisting of vibration and ultrasonic wave.

* * * * *

UNITED STATES PATENT AND TRADEMARK OFFICE
CERTIFICATE OF CORRECTION

PATENT NO. : 7,253,299 B2
APPLICATION NO. : 10/432288
DATED : August 7, 2007
INVENTOR(S) : Yasuhiro Iida, Hajime Manabe and Yasuyoshi Ueda It is certified that error appears in the above-identified patent and that said Letters Patent is hereby corrected as shown below:

On the title page, item (54) Title: delete "PROCESS FOR PURIFYING N2-(1(S)-ETHOXYCARBONYL-3-PHENYLPROPYL)-N6-THIFLUOROACETYL-L-LYSINE" and insert --PROCESS FOR PURIFYING $N^2$-(1(S)-ETHOXYCARBONYL-3-PHENYLPROPYL)-$N^6$-TRIFLUOROACETYL-L-LYSINE--

At column 1, line 49:
These impurities are, for instance, the diastereomer, i.e.,
$N^2$-(1(R)-ethoxycarbonyl-3-phenylpropyl)-$N^6$-trifluoro-acetyl-L-lysine of the formula (2):

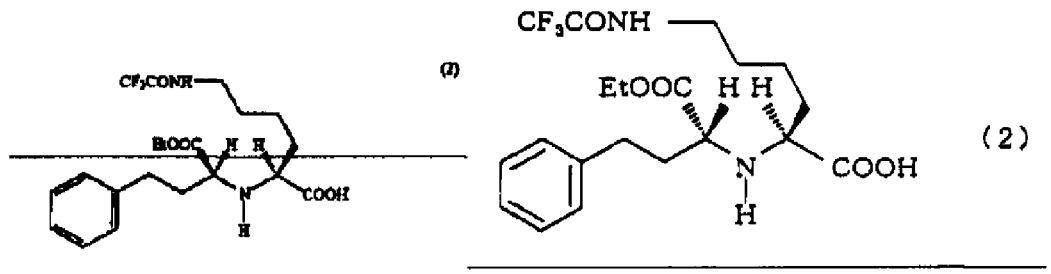

a cyclohexyl derivative, i.e.,
$N^2$-(1(S)-ethoxycarbonyl-3-cyclohexyl-propyl)-$N^6$-trifluoroacetyl-L-lysine of the formula (3):

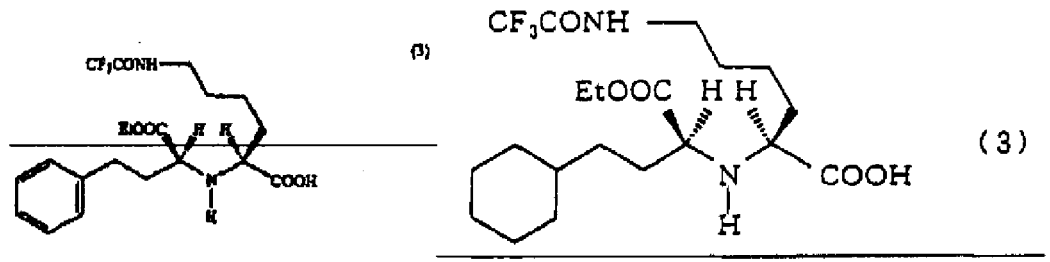

UNITED STATES PATENT AND TRADEMARK OFFICE
CERTIFICATE OF CORRECTION

PATENT NO.         : 7,253,299 B2  
APPLICATION NO. : 10/432288  
DATED                 : August 7, 2007  
INVENTOR(S)        : Yasuhiro Iida, Hajime Manabe and Yasuyoshi Ueda It is certified that error appears in the above-identified patent and that said Letters Patent is hereby corrected as shown below:

a carboxyl derivative, i.e.,
$N^2$-(1(S)-carboxy-3-phenylpropyl)-$N^6$-trifluoroacetyl-L-lysine of the formula (4):

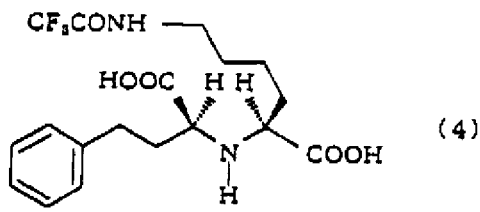

an ester derivative, i.e.,
$N^2$-(1(S)-ethoxycarbonyl-3-phenylpropyl)-$N^6$-trifluoroacetyl-L-lysine ester of the formula (5):

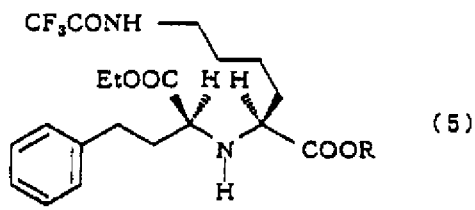

wherein R is an alkyl group, ethyl phenylbutyrate, and the like.

Signed and Sealed this

Eighth Day of December, 2009

David J. Kappos  
*Director of the United States Patent and Trademark Office*

UNITED STATES PATENT AND TRADEMARK OFFICE
CERTIFICATE OF CORRECTION

PATENT NO. : 7,253,299 B2
APPLICATION NO. : 10/432288
DATED : August 7, 2007
INVENTOR(S) : Yasuhiro Iida, Hajime Manabe and Yasuyoshi Ueda It is certified that error appears in the above-identified patent and that said Letters Patent is hereby corrected as shown below:

On the title page, item (54) and at Column 1, lines 1-4, Title: delete "PROCESS FOR PURIFYING N2-(1(S)-ETHOXYCARBONYL-3-PHENYLPROPYL)-N6-THIFLUOROACETYL-L-LYSINE" and insert --PROCESS FOR PURIFYING $N^2$-(1(S)-ETHOXYCARBONYL-3-PHENYLPROPYL)-$N^6$-TRIFLUOROACETYL-L-LYSINE--

At column 1, line 49:
These impurities are, for instance, the diastereomer, i.e.,
$N^2$-(1(R)-ethoxycarbonyl-3-phenylpropyl)-$N^6$-trifluoro-acetyl-L-lysine of the formula (2):

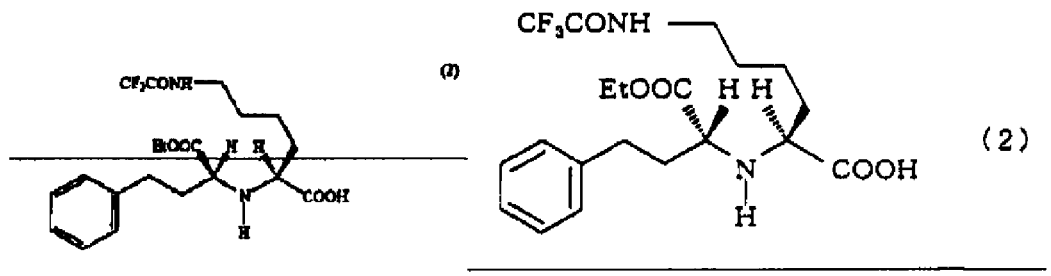

a cyclohexyl derivative, i.e.,
$N^2$-(1(S)-ethoxycarbonyl-3-cyclohexyl-propyl)-$N^6$-trifluoroacetyl-L-lysine of the formula (3):

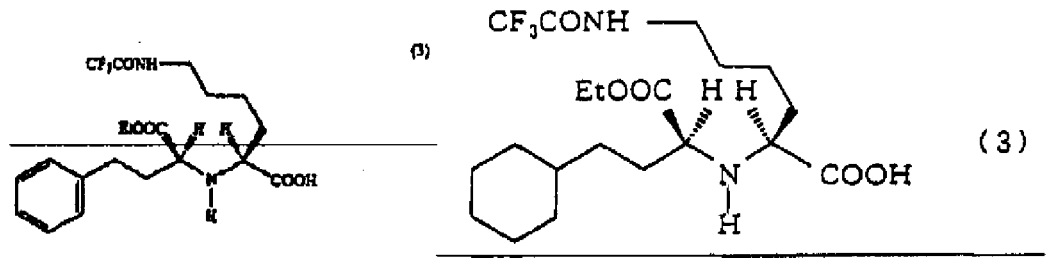

a carboxyl derivative, i.e.,
$N^2$-(1(S)-carboxy-3-phenylpropyl)-$N^6$-trifluoroacetyl-L-lysine of the formula (4):

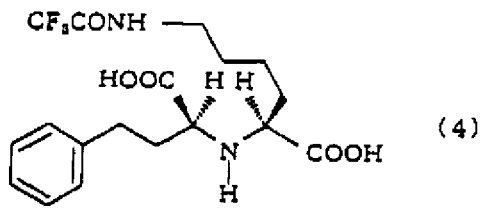

an ester derivative, i.e.,
$N^2$-(1(S)-ethoxycarbonyl-3-phenylpropyl)-$N^6$-trifluoroacetyl-L-lysine ester of the formula (5):

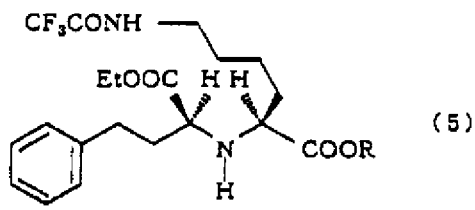

wherein R is an alkyl group, ethyl phenylbutyrate, and the like.

This certificate supersedes the Certificate of Correction issued December 8, 2009.

Signed and Sealed this

Twenty-sixth Day of January, 2010

David J. Kappos
*Director of the United States Patent and Trademark Office*